US008680038B2

(12) United States Patent
Balastre et al.

(10) Patent No.: US 8,680,038 B2
(45) Date of Patent: Mar. 25, 2014

(54) COPOLYMER CONTAINING ZWITTERIONIC UNITS AND OTHER UNITS, COMPOSITION COMPRISING THE COPOLYMER, AND USE

(75) Inventors: Marc Balastre, Paris (FR); Regan Crooks, London (GB); Chi-Thanh Vuong, Lognes (FR)

(73) Assignee: Rhodia Operations, Aubervilliers (FR)

( * ) Notice: Subject to any disclaimer, the term of this patent is extended or adjusted under 35 U.S.C. 154(b) by 795 days.

(21) Appl. No.: 12/097,494

(22) PCT Filed: Dec. 14, 2006

(86) PCT No.: PCT/EP2006/069730
§ 371 (c)(1),
(2), (4) Date: Feb. 18, 2009

(87) PCT Pub. No.: WO2007/068744
PCT Pub. Date: Jun. 21, 2007

(65) Prior Publication Data
US 2009/0197791 A1      Aug. 6, 2009

(30) Foreign Application Priority Data

Dec. 14, 2005   (FR) ..................................... 05 12670

(51) Int. Cl.
*C11D 3/37*     (2006.01)
(52) U.S. Cl.
CPC .................................. *C11D 3/3796* (2013.01)
USPC ............................ 510/475; 510/504; 524/815
(58) Field of Classification Search
USPC .................................. 510/475, 504; 524/815
See application file for complete search history.

(56) References Cited

U.S. PATENT DOCUMENTS

| | | |
|---|---|---|
| 3,308,067 A | 3/1967 | Diehl |
| 3,893,929 A | 7/1975 | Basadur |
| 3,959,230 A | 5/1976 | Hays |
| 4,075,131 A | 2/1978 | Sterling |
| 4,116,896 A | 9/1978 | Garrett et al. |
| 4,534,892 A | 8/1985 | Suzuki et al. |
| 4,565,647 A | 1/1986 | Llenado |
| 4,585,846 A * | 4/1986 | Schulz et al. ................. 526/264 |
| 4,597,898 A | 7/1986 | Meer |
| 4,607,076 A | 8/1986 | Schulz et al. |
| 4,702,857 A | 10/1987 | Gosselink |
| 4,711,730 A | 12/1987 | Gosselink et al. |
| 4,721,580 A | 1/1988 | Gosselink |
| 4,728,455 A | 3/1988 | Rerek |
| 4,746,456 A | 5/1988 | Kud et al. |
| 4,770,666 A | 9/1988 | Clauss |
| 4,877,896 A | 10/1989 | Gosselink |
| 4,968,451 A | 11/1990 | Scheibel et al. |
| 4,994,088 A | 2/1991 | Ando et al. |
| 5,026,490 A | 6/1991 | Peiffer et al. |
| 5,089,252 A | 2/1992 | Grollier et al. |
| 5,108,660 A | 4/1992 | Michael |
| 5,114,606 A | 5/1992 | Van Vliet et al. |
| 5,280,117 A | 1/1994 | Kerschaner et al. |
| 5,290,631 A | 3/1994 | Fleury et al. |
| 5,536,452 A | 7/1996 | Black |
| 5,559,261 A | 9/1996 | Sivik |
| 5,587,022 A | 12/1996 | Black |
| 6,346,588 B1 | 2/2002 | Fenchl et al. |
| 6,403,073 B1 | 6/2002 | Cauwet-Martin et al. |
| 6,410,671 B1 | 6/2002 | Argillier et al. |
| 7,378,033 B2 * | 5/2008 | Harrison et al. ............. 252/8.61 |
| 7,737,237 B2 * | 6/2010 | Destarac .................... 526/307.4 |
| 7,811,387 B2 * | 10/2010 | Scialla et al. ................. 134/25.2 |
| 7,838,588 B2 * | 11/2010 | Deroo et al. .................. 524/505 |
| 2006/0217285 A1 * | 9/2006 | Destarac ....................... 510/475 |
| 2006/0217286 A1 * | 9/2006 | Geoffroy et al. .............. 510/490 |
| 2008/0045420 A1 * | 2/2008 | Karagianni et al. .......... 507/121 |
| 2008/0255289 A1 * | 10/2008 | Deroo et al. .................. 524/442 |
| 2009/0029895 A1 * | 1/2009 | Scialla et al. ................. 510/180 |
| 2009/0197791 A1 * | 8/2009 | Balastre et al. ............... 510/407 |
| 2009/0301519 A1 * | 12/2009 | Aubay .............................. 134/6 |
| 2009/0306292 A1 * | 12/2009 | Bendejacq et al. ............. 525/55 |
| 2010/0093874 A1 * | 4/2010 | Monin et al. ................ 514/772.4 |
| 2010/0093929 A1 * | 4/2010 | Destarac ....................... 524/831 |
| 2010/0249267 A1 * | 9/2010 | Jiang et al. .................... 523/122 |
| 2010/0273697 A1 * | 10/2010 | Vuong et al. .................. 510/220 |
| 2010/0280169 A1 * | 11/2010 | Destarac ....................... 524/555 |

FOREIGN PATENT DOCUMENTS

| | | |
|---|---|---|
| EP | 011984 | 6/1980 |
| EP | 0066915 | 12/1982 |
| EP | 0112592 | 7/1984 |
| EP | 0488868 | 6/1992 |
| EP | 0532967 | 3/1993 |
| EP | 561656 | 9/1993 |
| EP | 0810239 | 12/1997 |
| EP | 0909809 | 4/1999 |
| FR | 2728915 | 7/1996 |

(Continued)

OTHER PUBLICATIONS

International Search Report, International Application No. PCT/EP2006/069730, dated Mar. 8, 2007, 4 pages.

Wen-Fu, L. at al.; "Poly(sulfobetaine)s and corresponding cationic polymers: 5 Synthesis and dilute aqueous solution properties of poly(sulfobetaine)s derived from acrylamide-maleic anhydride copolymer"; Sep. 1996, pp. 4389-4395, vol. 37, No. 19, Polymer, Elsevier Science Publishers, B.V. G.B.

Koberle, P. at al.; "Hydrophobically Modified Zwitterionic Polymers: Synthesis, Bulk Properties, and Miscibility with Inorganic Salts"; Received Nov. 9, 1993, Revised Manuscript Received Jan. 18, 1994; pp. 2165-2173; Macromolecules 1994 © 1994 American Chemical Society.

Castaño, V. M. at al.; "Evidence of ionic aggregates in some ampholytic polymers by transmission electron microscopy"; Received Nov. 9, 1988, accepted Oct. 13, 1989; pp. 654-657; vol. 5, No. 3, Mar. 1990; J. Mater. Res., © 1990 Materials Research Society.

(Continued)

*Primary Examiner* — Gregory Webb
(74) *Attorney, Agent, or Firm* — Hunton & Williams LLP

(57) ABSTRACT

The present invention provides a new copolymer comprising zwitterionic units and other units, a new composition comprising the copolymer, and the use of the copolymer or the compositions for treating or modifying surfaces.

21 Claims, No Drawings

(56) References Cited

FOREIGN PATENT DOCUMENTS

| FR | 2742657 | 6/1997 |
|---|---|---|
| GB | 1475798 A | 6/1977 |
| WO | WO 9216187 | 10/1992 |
| WO | WO 9623859 | 8/1996 |
| WO | WO 9623860 | 8/1996 |
| WO | WO 9623861 | 8/1996 |

OTHER PUBLICATIONS

Salamone, J. C. at al.; "Aqueous solution properties of a poly(vinyl imidazolium sulphobetaine)"; Received Jan. 30, 1978, revised Apr. 10, 1978; pp. 1157-1162; vol. 19; Polymer, 1978, © 1978 IPC Business Press.

Favresse, P. at al.; "New poly(carbobetaine)s made from zwitterionic diallylammonium monomers"; Received Jul. 13, 1998, revised Sep. 14, 1998; pp. 887-895; Macromol. Chem. Phys. 200, No. 4; © Wiley-VCH Verlag GmbH, D-69451 1999.

Soto, V. M.. at al.; "Poly(sulphopropylbetaines): 1. Synthesis and characterization"; Received Feb. 1, 1983; pp. 121-128; Polymer, 1984, vol. 25, January; © 1984.

Gauthier, et al.; "Sulfobetaine Zwitterionomers Based on n-Butyl Acrylate and 2-Ethoxyethyl Acrylate: Monomer Synthesis and Copolymerization Behavior"; pp. 511-523; vol. 40; Journal of Polymer Science: Part A: Polymer Chemistry; © 2002 John Wiley & Sons, Inc.

Lowe, et al.; "Synthesis and Properties of Low-Polydispersity Poly(sulfopropylbetaine)s and Their Block Copolymers"; Macromolecules, 32, 2141-2146 (1999).

Robinson, et al.; "Viscosity-Molecular weight relationship, intrinsic chain flexibility and dynamic solution properties of guar galactomannan"; pp. 17-32, Carbohydrate Research, 107, 1982.

Berlinova, et al. "Synthesis and aqueous solution behavior of copolymers containing sulfobetaine moieties in side chains", Received Feb. 22, 1999, received in revised from Apr. 5, 1999; accepted Apr. 8, 1999; pp. 831-837; Polymer 41 (20000); © Elsevier Science Ltd.

Hamaide, et al.; New polymeric phosphonato-, phosphinato- and carboxybetaïnes, 1; Syntheses and characterization by IR spectroscopy; pp. 1097-1107 Macromolecular Chemistry, 187 (1986).

* cited by examiner

COPOLYMER CONTAINING ZWITTERIONIC UNITS AND OTHER UNITS, COMPOSITION COMPRISING THE COPOLYMER, AND USE

CROSS-REFERENCE TO RELATED APPLICATIONS

This application is the U.S. National Stage filing of International Application No. PCT/EP2006/069730, filed Dec. 14, 2006, the disclosure of which is hereby incorporated by reference, which claims priority to FR-0512670, filed Dec. 14, 2005, the disclosure of which is hereby incorporated by reference.

FIELD OF THE INVENTION

The subject matter of the present invention is a novel copolymer comprising zwitterionic units and other units, a novel composition comprising the copolymer, and the use of the copolymer or compositions in the treatment or modification of surfaces. The copolymer, the composition and the use exhibit in particular a particular advantage in the field of cosmetics, in particular for producing shampoos, conditioners or shower gels or for conditioning the skin and/or hair. They are also advantageous in the field of detergency, in particular for domestic, industrial or institutional care purposes.

BACKGROUND OF THE INVENTION

Polymers, homopolymers or copolymers, comprising zwitterionic units are known. Uses in various industrial fields of compositions of such polymers are known.

For example, copolymers comprising units having carboxybetaine groups or having sulfobetaine groups are known.

The document U.S. Pat. No. 4,075,131 describes polymers and their introduction into conditioning shampoos. Polymers described are homopolymers comprising zwitterionic units deriving from monomers of the family of the carboxybetaines. They are carboxybetaine homopolymers.

The document U.S. Pat. No. 6,403,073 describes cosmetic compositions intended to be applied to the hair, such as shampoos, comprising a polyorganosiloxane (silicone) and an insoluble polyampholyte polymer. The document describes in particular homopolymers comprising betaine zwitterionic units. A comonomer which can be used in copolymerization with the betaine monomers is not described.

The document FR 2 742 657 describes cosmetic compositions intended to be applied to the hair, such as shampoos, comprising a cationic polymer with a charge density of less than or equal to 4 meq/g and an insoluble polyampholyte polymer identical to that of the document U.S. Pat. No. 4,075,131.

The document U.S. Pat. No. 4,534,892 describes compositions, such as shampoos, comprising a copolymer comprising betaine units, crosslinking units and optionally other units. Sulfobetaine monomers are mentioned as possible betaine comonomers. The examples disclose copolymers comprising cationic units derived from QDM (2-methacryloyl-oxyethyltrimethylammonium, ethosulfate counterion) and acrylic acid or AMPS units (anionic or potentially anionic monomers) and units of a crosslinking monomer.

The document EP 112 592 describes polymers which can comprise betaine units and their use in detergent compositions (laundry detergents). In particular, the document describes the family of the polyacrylates, polyacrylamides, comprising betaine units, of formula IV, page 16. It should be noted that these are homopolymers comprising betaine units.

The document FR 2 519 863 describes compositions comprising a cationic compound (cationic surfactant or cationic polymer) and a betainized polymer. The betainized polymer comprises betaine units of carboxybetaine type. It is obtained by postpolymerization reaction, by reaction of a compound of formula $XCH_2COO^-$ with a polymer comprising units carrying a tertiary amine (potentially cationic) group. An example is the polymer Amersette (Amerchol) or the polymer Amphoset (Mitsubishi Petrochem.).

The document U.S. Pat. No. 4,994,088 describes hair compositions, of lacquer type, or more generally products for styling the hair. The compositions comprise a polymer having betaine units. In examples 5 and 6, sulfobetaine homopolymers are described.

The document U.S. Pat. No. 4,607,076 describes copolymers comprising sulfobetaine units, for example units deriving from SPE, and vinylpyrrolidone units. The copolymers are used as viscosifying agents in saline compositions.

The document EP 532 967 describes cosmetic compositions, for example shampoos, comprising copolymers of formula (1) comprising betaine units (index n) and hydrophobic units (index m). The betaine units are carboxybetaines.

The document WO 2004/083354 describes compositions for cleaning hard surfaces comprising polymers having betaine units. The document suggests copolymers comprising, in addition to the betaine units, anionic units.

The document WO 00/01746 describes copolymers based on acrylamide and on sulfobetaines or on phosphobetaines. It is indicated in this document that these copolymers are effective as viscosifying agents and as agents which modify the surfaces of suspended particles in the field of the oil industry.

The document U.S. Pat. No. 5,026,490 describes other copolymers comprising sulfobetaine units and their use as deflocculating agents for drilling muds in the oil industry. The document U.S. Pat. No. 6,346,588 describes other copolymers comprising sulfobetaine units, the formulation of which in a drilling fluid is facilitated. The document U.S. Pat. No. 4,607,076 describes other copolymers comprising sulfobetaine units and their use in the oil industry as viscosifying agents in the presence of brine.

Furthermore, it is known that the formation of coacervates is favorable to the treatment or modification of surfaces, in particular for conditioning the hair and/or skin. Thus, the use of cationic derivatives of polysaccharides in shampoos comprising anionic surfactants, preferably in combination with conditioning agents, such as polyorganosiloxanes, is known. It has been taught that the formation of coacervates promotes conditioning. The ranges of formulations where it is possible to observe coacervate formation are generally limited and generally depend on the nature and amounts of the surfactants and polymers employed. There exists a need for novel polymers which can in particular participate in the formation of coacervates in modified or extended ranges of formulations.

Furthermore, there exists, in industry, a constant need for novel polymers which can contribute novel properties to compositions or improve properties.

SUMMARY OF THE INVENTION

The invention meets at least one of the above-mentioned needs by providing a copolymer comprising zwitterionic units A and other units B, the units A comprising a betaine group, characterized in that:

the units B are cationic or potentially cationic units, and
the betaine group of the units A is a sulfobetaine or phosphobetaine group.

The invention also relates to compositions comprising the copolymer.

According to preferred form, the composition comprises coacervates or is capable of forming coacervates.

The invention also relates to coacervates comprising the copolymer.

The invention also relates to the use of the copolymer in compositions.

The invention also relates to a process for the treatment or modification of a surface, comprising the following stages:
applying, to the surface, a composition comprising the copolymer, and
optionally removing the carrier or diluting the composition or modifying the pH.

The invention also relates to the surface thus treated or modified.

The invention also relates to a substrate, the surface of which comprises the copolymer, for example in the form of coacervates.

The copolymer can be deposited or promote the deposition of an agent for surface treatment or modification. In particular, in a cosmetic composition, for example in shampoos, conditioners or shower gels, it can provide modified or improved condition of the hair and/or skin. It can promote the deposition of conditioning agents, such as polyorganosiloxanes. The cosmetic composition can in particular clean and condition while providing better combing on wet hair. In order to be able to clean, large amounts of anionic, nonionic and/or amphoteric surfactants are generally used in the composition. Conditioning is obtained by the introduction of the copolymer, which forms a coating on the hairs. Silicone oils can also be added. It is known that the deposition of polymers and of active principles (silicone oils, and the like) present in a shampoo can be improved by the formation of coacervates between a cationic polymer and anionic surfactants. The copolymer according to the invention can in particular make possible the formation of coacervates in the composition in the presence of surfactants. It has been found in particular that this formation can be promoted by varying parameters, such as the nature and composition of the copolymer and ingredients present in the composition. The composition of the copolymer and its amount can be optimized in order to obtain a composition which is transparent and precipitates (with formation of coacervates, for example) on diluting. The copolymers according to the invention can be extensively adjusted. They can in particular comprise nonionic units which can enhance their ability to be formulated in different formulations and/or for different formulations. Their modular nature allows them to be formulated in different environments; it also makes it possible to adjust the properties and performances of the compositions into which they are introduced.

DETAILED DESCRIPTION

Definitions

In the present patent application, copolymer denotes any polymer comprising at least two types of units. The term "copolymer" comprises binary copolymers, comprising only two types of units, copolymers comprising three types of units (terpolymers), and the like.

In the present patent application, unit deriving from a monomer denotes, for the units other than the units A, a unit which can be obtained directly from said monomer by polymerization. Thus, for example, a unit deriving from an acrylic or methacrylic acid ester does not cover a unit of formula —$CH_2$—CH(COOH)—, —$CH_2$—C($CH_3$)(COOH)— or —$CH_2$CH(OH)—, respectively, obtained, for example, by polymerizing an acrylic or methacrylic acid ester or vinyl acetate respectively and by then hydrolyzing. A unit deriving from acrylic or methacrylic acid covers, for example, a unit obtained by polymerizing a monomer (for example an acrylic or methacrylic acid ester) and by then reacting (for example by hydrolysis) the polymer obtained so as to obtain units of formula —$CH_2$—CH(COOH)— or —$CH_2$—C($CH_3$)(COOH)—. A unit deriving from a vinyl alcohol covers, for example, a unit obtained by polymerizing a monomer (for example a vinyl ester) and by then reacting (for example by hydrolysis) the polymer obtained so as to obtain units of formula —$CH_2$—CH(OH)—.

In the present patent application, the term "hydrophobic" is used in its normal sense of "which does not have an affinity for water"; this means that the organic polymer of which it is composed, taken alone (with the same composition and with the same molar mass), would form a two-phase macroscopic solution in distilled water at 25° C. at a concentration of greater than 1% by weight.

In the present patent application, the terms "hydrophilic", "water-soluble" and "water dispersible", are also used in their normal sense of "which has an affinity for water", that is to say is not capable of forming a two-phase macroscopic solution in distilled water at 25° C. at a concentration of greater than 1% by weight.

Cationic or potentially cationic units B is understood to mean units which comprise a cationic or potentially cationic group. Cationic units or groups are units or groups which exhibit at least one positive charge (generally in association with one or more anions, such as the chloride ion, the bromide ion, a sulfate group or a methyl sulfate group), whatever the pH of the medium into which the copolymer is introduced. Potentially cationic units or groups are units or groups which can be neutral or can exhibit at least one positive charge depending on the pH of the medium into which the copolymer is introduced. In this case, reference will be made to potentially cationic units in the neutral form or in the cationic form. By extension, it is possible to speak of cationic or potentially cationic monomers.

Anionic or potentially anionic units $C_A$ means units which comprise an anionic or potentially anionic group. Anionic units or groups are units or groups which exhibit at least one negative charge (generally in association with one or more cations, such as cations of alkali metal or alkaline earth metal compounds, for example sodium, or with one or more cationic compounds, such as ammonium), whatever the pH of the medium in which the copolymer is present. Potentially anionic units or groups are units or groups which can be neutral or can exhibit at least one negative charge depending on the pH of the medium in which the copolymer is present. In this case, reference will be made to potentially anionic units $A_A$ in the neutral form or in the anionic form. By extension, it is possible to speak of anionic or potentially anionic monomers.

Neutral units $C_N$ means units which do not exhibit a charge, whatever the pH of the medium in which the copolymer is present.

In the present patent application, unless otherwise indicated, when reference is made to molar mass, it will relate to the absolute weight-average molar mass, expressed in g/mol. This can be determined by aqueous gel permeation chromatography (GPC), by light scattering (DDL or also MALLS), with an aqueous eluent or an organic eluent (for example, dimethylacetamide, dimethylformamide, and the like), depending on the composition of the polymer.

In the present patent application, "mean charge Q of a copolymer" denotes the charge defined by the following equation:

$$Q = \frac{[b]X_B - [c_A]X_{C_A}}{[b]X_B + [c_A]X_{C_A}}$$

where:
[b] is the molar concentration of units B in the copolymer,
[$c_A$] is the molar concentration of units $A_A$ in the part A,
$X_B$ represents the degree of possible neutralization of the units B (in the case where the units B are potentially cationic); $X_B=[BH^+]/([B]+[BH^+])$,
$X_{C_A}$ represents the degree of possible neutralization of the units $C_A$ (in the case where the units $C_A$ are potentially anionic); $X_{C_A}=[C_A]/([C_AH]+[C_A])$.

In the present patent application, "coacervatee" denotes a complex of the copolymer and of a surfactant. The presence of coacervatee phases can be determined by the known techniques referring to physicochemical objects of this type. For example, it is possible to carry out analyses with a microscope of the composition or of the dilute composition. A coacervate phase can be identified as a phase emulsified in the composition, if appropriate as an additional phase after diluting or modifying the composition (for example, modifying the pH). Use may be made of dyes in order to distinguish the coacervate phases from other phases dispersed in the composition. A method by measurement of transmission is in particular described in the examples.

Copolymer

The copolymer according to the invention comprises at least two types of units, A and B. The polymer is preferably a random, preferably linear, copolymer. It can also be:
- a gradient copolymer,
- a comb copolymer,
- a block copolymer comprising a block comprising units A and a block comprising units B,
- a block copolymer comprising a block comprising units A and B and a different block not simultaneously comprising units A and units B, preferably a different block comprising:
  hydrophilic or hydrophobic nonionic units $C_N$, and/or
  anionic or potentially anionic units $C_A$.

In the context of a comb copolymer, the copolymer can exhibit a backbone comprising units A and side macromolecular chains exhibiting units B.

The copolymer can in particular comprise, in addition to the units A and B:
hydrophilic or hydrophobic nonionic units $C_N$, and/or
anionic or potentially anionic units $C_A$.

The molar ratio of the units A to the units B is between 99/1 and 1/99, preferably between 95/5 and 5/95, more preferably between 90/10 and 10/90. According to one embodiment, the ratio of the units A to the units B is greater than 50/50. According to another form, this same ratio is less than 50/50.

The units A and B advantageously represent from 1 to 100 mol %, preferably from 1 to 95 mol %, of the units of the copolymer. According to an advantageous form, the copolymer comprises at least 5 mol % of hydrophilic or hydrophobic, preferably hydrophilic, nonionic units $C_N$.

In general, the charges (charges carried in particular by the units B and A) present in the copolymer are carried by pendent groups.

Units A

As 1st group of units, the copolymer comprises units A comprising a sulfobetaine or phosphobetaine group which comprises a cationic group and a sulfur-comprising or phosphorus-comprising anionic group. Within these units, the number of positive charges is equal to the number of negative charges. The units A are electrically neutral, in at least one pH range. This permanent anionic charge can be contributed by one or more sulfonate, phosphate, phosphonate or phosphinate anions. The cationic charge can be contributed by one or more onium or inium cations of the nitrogen (ammonium, pyridinium, imidazolinium cations), phosphorus (phosphonium, and the like) or sulfur (sulfonium, and the like) family.

Preferably, the betaine groups of the units A are pendent groups of the copolymer (they are arranged in comb fashion along the macromolecular chain of the polymer).

The betaine groups can be represented, in the case of the cations of the nitrogen family, by the following formulae (I) to (IV), exhibiting a cationic charge at the center of the functional group and an anionic charge at the end of the functional group, and of following formula (V), exhibiting an anionic charge at the center of the functional group and a cationic charge at the end of the functional group:

  (I)

  (II)

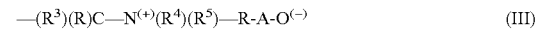  (III)

  (IV)

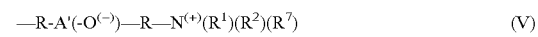  (V)

in which formulae (I) to (IV):
the symbols $R^1$, $R^2$ and $R^5$, which are alike or different, represent an alkyl radical comprising from 1 to 7 carbon atoms, preferably from 1 to 2 carbon atoms
the symbols $R^3$ and $R^4$ represent hydrocarbon radicals forming, with the nitrogen atom, a nitrogenous heterocycle optionally comprising one or more other heteroatoms, in particular nitrogen
the symbol $R^6$ represents a hydrocarbon radical forming, with the nitrogen atom, a saturated or unsaturated nitrogenous heterocycle optionally comprising one or more other heteroatoms, in particular nitrogen
the symbol R represents a linear or branched alkylene radical comprising from 1 to 15 carbon atoms, preferably from 2 to 4 carbon atoms, optionally substituted by one or more hydroxyl groups, or a benzylene radical
the symbol A represents S(=O)(=O), OP(=O)(=O), OP(=O)(OR'), P(=O)(OR') or P(=O)(R'), where R' represents an alkyl radical comprising from 1 to 7 carbon atoms or a phenyl radical
in which formula (V),
the symbols $R^1$ and $R^2$ have the definition given above
the symbol $R^7$, which is identical to or different from $R^1$ or $R^2$, represents an alkyl radical comprising from 1 to 7 carbon atoms, preferably from 1 to 2 carbon atoms
the symbol A' represents —O—P(=O)—O—.

In the case of cations of the phosphorus family, mention may be made of the betaine groups of formulae (VI) and (VII);

  (VI)

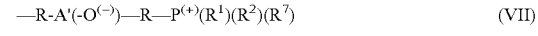  (VII)

in which formula (VI) the symbols $R^1$, $R^2$, R and A have the definition given above in which formula (VII):
   the symbols $R^1$, $R^2$, $R^7$ and R have the definition given above
   the symbol A' represents —O—P(=O)—O—.

In the case of cations of the sulfur family, mention may be made of the betaine groups of formulae (VIII) and (IX):

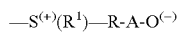  (VIII)

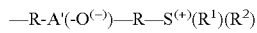  (IX)

in which formula (VIII) the symbols $R^1$, R and A have the definition given above in which formula (IX):
   the symbols $R^1$, $R^2$ and R have the definition given above
   the symbol A' represents —O—P(=O)—O—.

The units A and B, optionally with other units, preferably form a polyalkylene hydrocarbon chain (also known as backbone) optionally interrupted by one or more nitrogen or sulfur atoms.

The betaine groups can be connected to the carbon atoms of a hydrocarbon chain of the polymer via in particular a divalent or polyvalent hydrocarbon unit (for example, alkylene or arylene) optionally interrupted by one or more heteroatoms, in particular oxygen, an ester unit, an amide unit, or else by a valency bond.

In the copolymer, the body of units comprising a betaine group can be composed of identical or different units.

The copolymer can in particular be obtained by radical polymerization in aqueous solution of monomers comprising monomers which can result in units B and monomers comprising an ethylenically unsaturated betaine group, in particular ethylenically unsaturated monomers carrying at least one betaine group of above formulae (I) to (IX).

Said monomers can exhibit, by way of example:
   one or more mono- or polyethylenically unsaturated hydrocarbon radicals (in particular vinyl, allyl, styryl, and the like),
   one or more mono- or polyethylenically unsaturated ester radicals (in particular acrylate, methacrylate, maleate, and the like), and/or
   one or more mono- or polyethylenically unsaturated amide radicals (in particular acrylamido, methacrylamido, and the like).

The units A can derive from at least one betaine monomer selected from the group consisting of the following monomers:
   alkylsulfonates or -phosphonates of dialkylammonioalkyl acrylates or methacrylates, -acrylamides or -methacrylamides, such as:
      sulfopropyldimethylammonioethyl methacrylate, sold by Raschig under the name SPE:

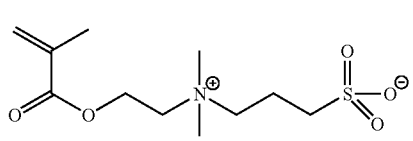  (SPE)

sulfoethyldimethylammonioethyl methacrylate and sulfobutyldimethylammonioethyl methacrylate:

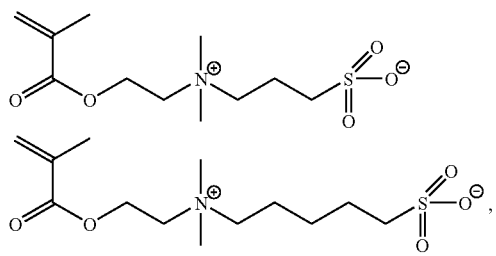

the synthesis of which is described in the paper "Sulfobetaine zwitterionomers based on n-butyl acrylate and 2-ethoxyethyl acrylate: monomer synthesis and copolymerization behavior", Journal of Polymer Science, 40, 511-523 (2002), sulfohydroxypropyldimethylammonioethyl methacrylate:

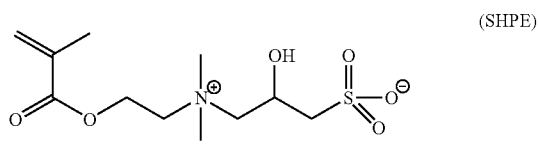 [SMILES: C=C(C)C(=O)OCC[N+](C)(C)CC(O)CS(=O)(=O)[O-]]  (SHPE)

sulfopropyldimethylammoniopropylacrylamide:

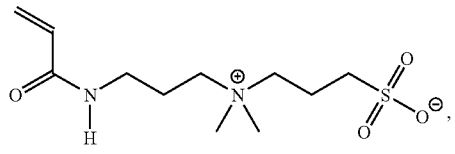 [SMILES: C=CC(=O)NCCC[N+](C)(C)CCCS(=O)(=O)[O-]]

the synthesis of which is described in the paper "Synthesis and solubility of the poly(sulfobetaine)s and the corresponding cationic polymers: 1. Synthesis and characterization of sulfobetaines and the corresponding cationic monomers by nuclear magnetic resonance spectra", Wen-Fu Lee and Chan-Chang Tsai, Polymer, 35 (10), 2210-2217 (1994), sulfopropyldimethylammoniopropylmethacrylamide, sold by Raschig under the name SPP:

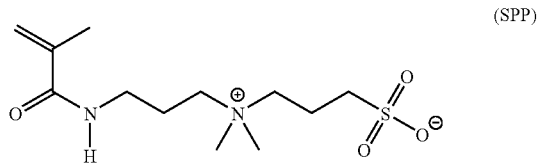 [SMILES: C=C(C)C(=O)NCCC[N+](C)(C)CCCS(=O)(=O)[O-]]  (SPP)

sulfohydroxypropyldimethylammoniopropyl-methacrylamide:

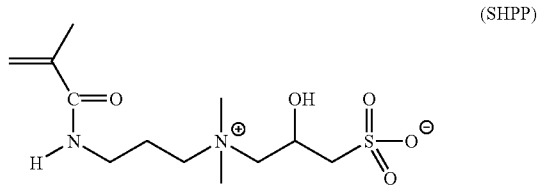 [SMILES: C=C(C)C(=O)NCCC[N+](C)(C)CC(O)CS(=O)(=O)[O-]]  (SHPP)

sulfopropyldiethylammonioethyl methacrylate:

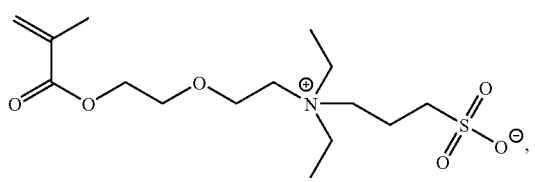 [SMILES: C=C(C)C(=O)OCCOCC[N+](CC)(CC)CCCS(=O)(=O)[O-]]

the synthesis of which is described in the paper "Poly(sulphopropylbetaines): 1. Synthesis and characterization", V. M. Monroy Soto and J. C. Galin, Polymer, 1984, Vol. 25, 121-128, sulfohydroxypropyldiethylammonioethyl methacrylate:

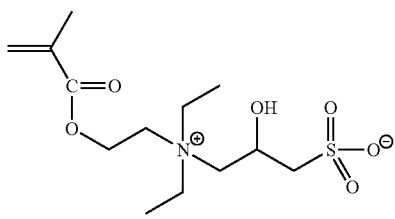 [SMILES: C=C(C)C(=O)OCC[N+](CC)(CC)CC(O)CS(=O)(=O)[O-]]

heterocyclic betaine monomers, such as:
sulfobetaines derived from piperazine:

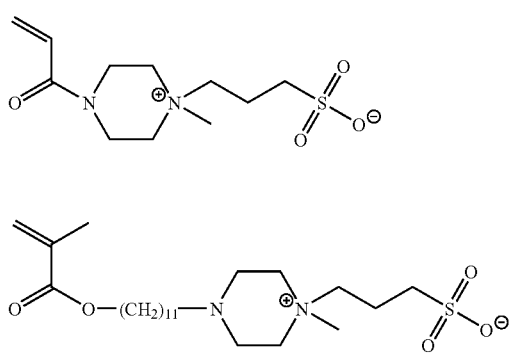

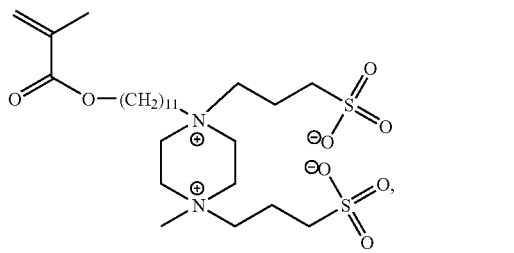

the synthesis of which is described in the paper "Hydrophobically Modified Zwitterionic Polymers: Synthesis, Bulk Properties, and Miscibility with Inorganic Salts", P. Koberle and A. Laschewsky, Macromolecules, 27, 2165-2173 (1994), sulfobetaines derived from 2-vinylpyridine and 4-vinylpyridine, such as
2-vinyl-1-(3-sulfopropyl)pyridinium betaine (2SPV), sold by Raschig under the name SPV:

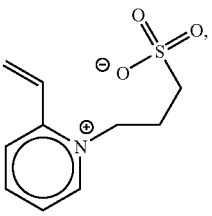

(2SPV)

4-vinyl-1-(3-sulfopropyl)pyridinium betaine (4SPV), the synthesis of which is disclosed in the paper "Evidence of ionic aggregates in some ampholytic polymers by transmission electron microscopy", V. M. Castaño and A. E. González, J. Cardoso, O. Manero and V. M. Monroy, J. Mater. Res., 5 (3), 654-657 (1990):

(4SPV)

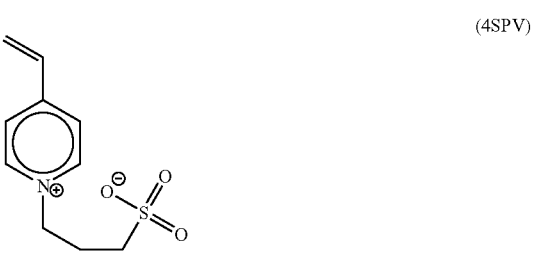

1-vinyl-3-(3-sulfopropyl)imidazolium betaine:

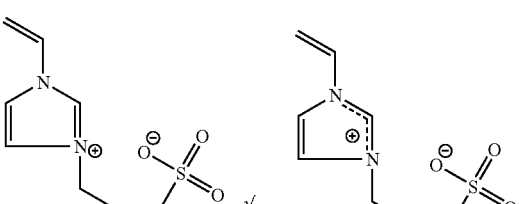

the synthesis of which is described in the paper "Aqueous solution properties of a poly(vinyl imidazolium sulphobetaine)", J. C. Salamone, W. Volkson, A. P. Oison, S. C. Israel, Polymer, 19, 1157-1162 (1978), alkylsulfonates or -phosphonates of dialkylammonioalkylallylics, such as sulfopropyl-methyldiallylammonium betaine:

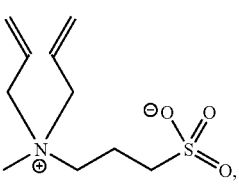

the synthesis of which is described in the paper "New poly (carbobetaine)s made from zwitterionic diallylammonium monomers", Favresse, Philippe; Laschewsky, Andre, Macromolecular Chemistry and Physics, 200(4), 887-895 (1999), alkylsulfonates or -phosphonates of dialkylammonioalkylstyrenes, such as:

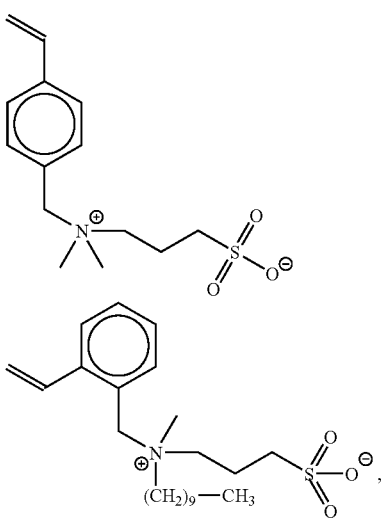

the synthesis of which is described in the paper "Hydrophobically Modified Zwitterionic Polymers: Synthesis, Bulk Properties, and Miscibility with Inorganic Salts", P. Koberle and A. Laschewsky, Macromolecules, 27, 2165-2173 (1994), betaines resulting from ethylenically unsaturated anhydrides and dienes, such as:

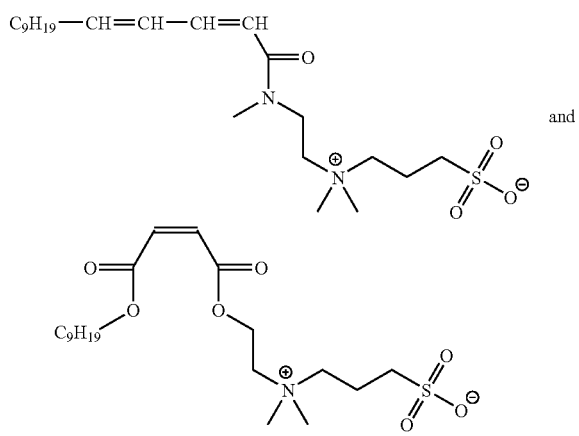

and the synthesis of which is described in the paper "Hydrophobically Modified Zwitterionic Polymers: Synthesis, Bulk Properties, and Miscibility with Inorganic Salts", P. Koberle and A. Laschewsky, Macromolecules, 27, 2165-2173 (1994), phosphobetaines, such as:

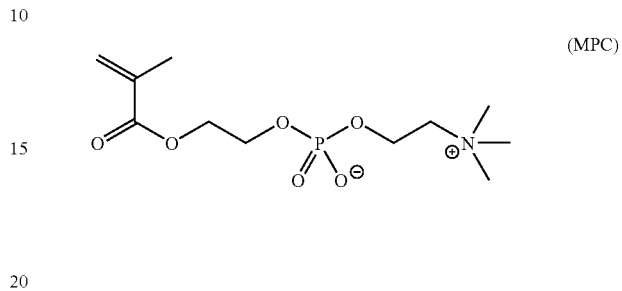

(MPC)

or alternatively:

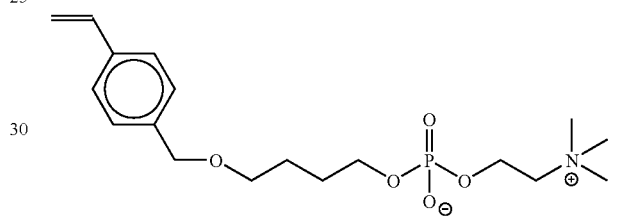

(VPC)

The synthesis of MPC and of VPC is described in EP 810 239 B1 (Biocompatibles, Alister et al.).

The polymer according to the invention can also be obtained in a known way by chemical modification of a polymer referred to as a precursor polymer. Thus, sulfobetaine units can be obtained by chemical modification of units of a precursor polymer, preferably by chemical modification of a polymer comprising pendent amine functional groups, using a sulfonated electrophilic compound, preferably a sultone (propane sultone, butane sultone) or a haloalkylsulfonate.

A few synthetic examples are given below:

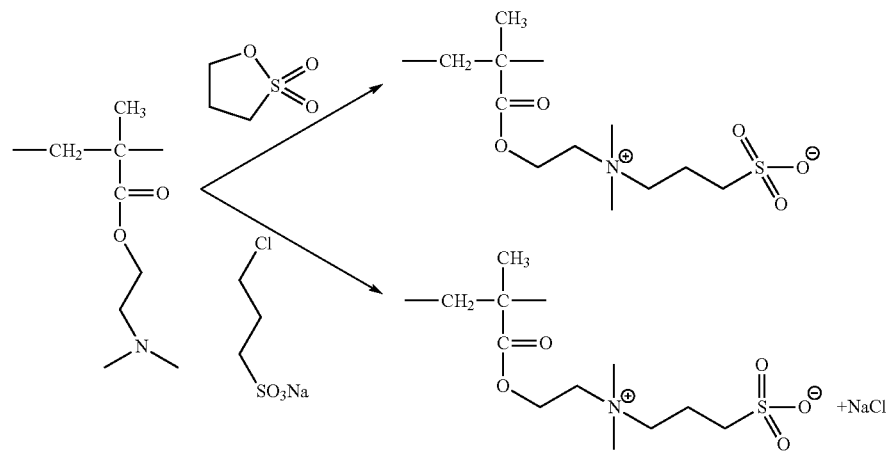

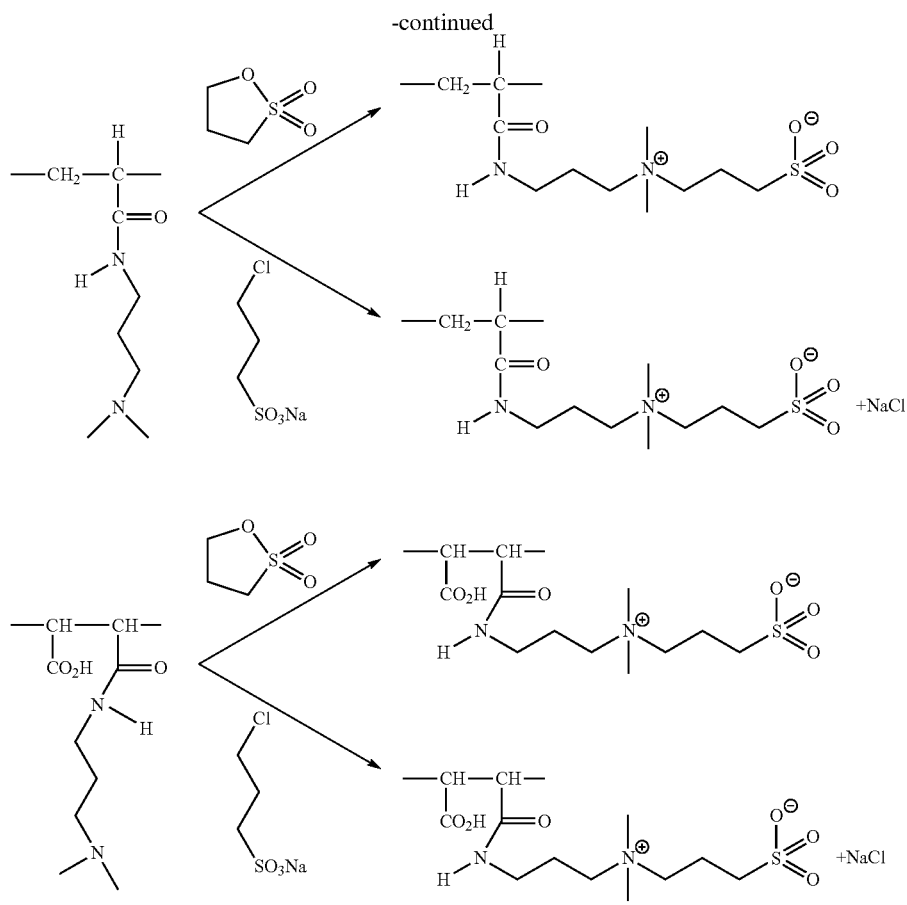

The main routes of access by chemical modification of a precursor polymer by sultones and haloalkylsulfonates are described in particular in the following documents:
- "Synthesis and aqueous solution behavior of copolymers containing sulfobetaine moieties in side chains", I. V. Berlinova, I. V. Dimitrov, R. G. Kalinova, N. G. Vladimirov, Polymer, 41, 831-837 (2000)
- "Poly(sulfobetaine)s and corresponding cationic polymers: 3. Synthesis and dilute aqueous solution properties of poly(sulfobetaine)s derived from styrene-maleic anhydride", Wen-Fu Lee and Chun-Hsiung Lee, Polymer, 38 (4), 971-979 (1997)
- "Poly(sulfobetaine)s and corresponding cationic polymers. VIII. Synthesis and aqueous solution properties of a cationic poly(methyl iodide quaternized styrene-N,N-dimethylaminopropyl maleamidic acid) copolymer", Lee, Wen-Fu and Chen, Yan-Ming, Journal of Applied Polymer Science, 80, 1619-1626 (2001)
- "Synthesis of polybetaines with narrow molecular mass distribution and controlled architecture", Andrew B. Lowe, Norman C. Billingham and Steven P. Armes, Chem. Commun., 1555-1556 (1996)
- "Synthesis and Properties of Low-Polydispersity Poly(sulfopropylbetaine)s and Their Block Copolymers", Andrew B. Lowe, Norman C. Billingham and Steven P. Armes, Macromolecules, 32, 2141-2146 (1999)
- Japanese patent application published on Dec. 21, 1999 under the number 11-349826.
  The preparation of polyphosphonato- and phosphinatobetaines by chemical modification is reported in "New polymeric phosphonato-, phosphinato- and carboxybetaines", T. Hamaide, Macromolecular Chemistry, 187, 1097-1107 (1986).

According to a preferred embodiment, the units A exhibit one of the following formulae:

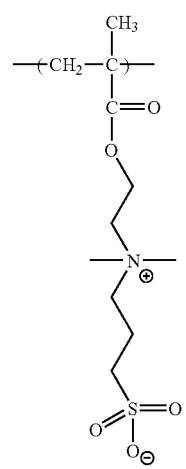

-(SPE)-

-continued

-(SPP)-

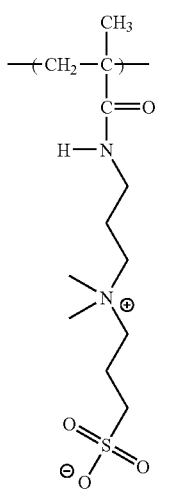

-(SHPE)-

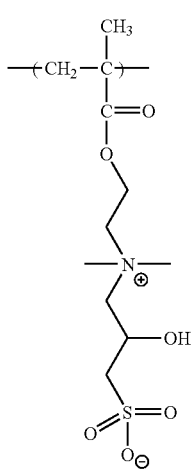

-(SHPP)-

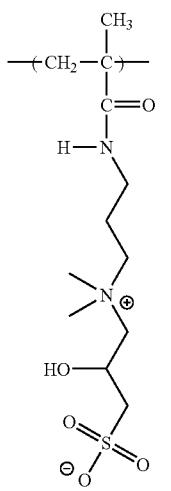

Units B

The units B are cationic or potentially cationic units comprising 1, 2, 3 or more cationic or potentially cationic groups in the chain forming the backbone of the copolymer or in the side position with respect to the chain forming the backbone of the copolymer.

The cationic units B are preferably units comprising at least one quaternary ammonium group. The potentially cationic units B can be units comprising at least one tertiary amine group.

Mention may be made, as examples of potentially cationic monomers B from which the units B can derive, of:

ω-(N,N-dialkylamino)alkylamides of α,β-monoethylenically unsaturated carboxylic acids, such as N,N-dimethylaminomethylacrylamide or -methacrylamide, [2-(N,N-dimethylamino)ethyl]-acrylamide or -methacrylamide, [3-(N,N-dimethylamino)propyl]acrylamide or -methacrylamide or [4-(N,N-dimethylamino)butyl]acrylamide or -methacrylamide α,β-monoethylenically unsaturated aminoesters, such as 2-(dimethylamino)ethyl acrylate (ADAM), 2-(dimethylamino)ethyl methacrylate (DMAM), 3-(dimethylamino)propyl methacrylate, 2-(tert-butylamino)ethyl methacrylate, 2-(dipentyl-amino)ethyl methacrylate or 2-(diethylamino)ethyl methacrylate vinylpyridines vinylamine vinylimidazolines precursor monomers of amine functional groups, such as N-vinylformamide, N-vinylacetamide, and the like, which generate primary amine functional groups by simple acidic or basic hydrolysis.

Mention may be made, as examples of cationic monomers B from which the units B can derive, of:

ammoniumacryloyl or -acryloyloxy monomers, such as:

trimethylammoniopropyl methacrylate chloride, trimethylammonioethylacrylamide or -methacrylamide chloride or bromide, trimethylammoniobutylacrylamide or -methacrylamide methyl sulfate, trimethylammoniopropylmethacrylamide methyl sulfate (MES), (3-methacrylamidopropyl)trimethylammonium chloride (MAPTAC), (3-acrylamidopropyl)trimethylammonium chloride (APTAC), methacryloyloxyethyltrimethylammonium chloride or methyl sulfate, acryloyloxyethyltrimethylammonium chloride or acryloyloxyethyltrimethylammonium methyl sulfate (ADAMQUAT Cl or ADAMQUAT MeS), methyldiethylammonioethyl acrylate methyl sulfate (ADAEQUAT MeS), benzyldimethylammonioethyl acrylate chloride or methyl sulfate (ADAMQUAT BZ 80), 1-ethyl-2-vinylpyridinium or 1-ethyl-4-vinylpyridinium bromide, chloride or methyl sulfate, N,N-dialkyldiallylamine monomers, such as N,N-dimethyldiallylammonium chloride (DADMAC), the chloride of dimethylaminopropylmethacrylamide, N-(3-chloro-2-hydroxypropyl)trimethylammonium (DIQUAT chloride), the methyl sulfate of dimethylamino-propylmethacrylamide, N-(3-(methyl sulfate)-2-hydroxypropyl)trimethylammonium (DIQUAT methyl sulfate), the monomer of formula:

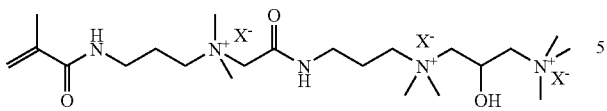

where X⁻ is an anion, preferably chloride or methyl sulfate.

Mention may be made, as examples of potentially cationic monomers B from which the units B can derive, of:
- ω-(N,N-dialkylamino)alkylamides of α,β-monoethylenically unsaturated carboxylic acids, such as N,N-dimethylaminomethylacrylamide or -methacrylamide, [2-(N,N-dimethylamino)ethyl]-acrylamide or -methacrylamide, [3-(N,N-dimethylamino)propyl]acrylamide or -methacrylamide or [4-(N,N-dimethylamino)butyl]acrylamide or -methacrylamide
- α,β-monoethylenically unsaturated aminoesters, such as 2-(dimethylamino)ethyl acrylate (ADAM), 2-(dimethylamino)ethyl methacrylate (DMAM), 3-(dimethylamino)propyl methacrylate, 2-(tert-butylamino)ethyl methacrylate, 2-(dipentyl-amino)ethyl methacrylate or 2-(diethylamino)ethyl methacrylate
- vinylpyridines
- vinylamine
- vinylimidazolines
- precursor monomers of amine functional groups, such as N-vinylformamide, N-vinylacetamide, and the like, which generate primary amine functional groups by simple acidic or basic hydrolysis.

Units C

Mention may be made, as examples of hydrophobic nonionic monomers $C_N$ from which the hydrophobic units $C_N$ can derive, of:
- vinylaromatic monomers, such as styrene, α-methylstyrene, vinyltoluene, and the like,
- vinyl or vinylidene halides, such as vinyl chloride or vinylidene chloride,
- $C_1$-$C_{12}$ alkyl esters of α,β-monoethylenically unsaturated acids, such as methyl acrylate, ethyl acrylate, butyl acrylate, methyl methacrylate, ethyl methacrylate, butyl methacrylate, 2-ethylhexyl acrylate, and the like,
- vinyl or allyl esters of saturated carboxylic acids, such as vinyl acetate, allyl acetate, vinyl propionate, allyl propionate, vinyl versatate, allyl versatate, vinyl stearate, allyl stearate, and the like,
- α,β-monoethylenically unsaturated nitriles comprising from 3 to 12 carbon atoms, such as acrylonitrile, methacrylonitrile, and the like,
- α-olefins, such as ethylene, and the like,
- conjugated dienes, such as butadiene, isoprene or chloroprene,
- diethylene glycol ethyl ether acrylate or diethylene glycol ethyl ether methacrylate.

Mention may be made, as examples of hydrophilic nonionic monomers $C_N$ from which the hydrophilic nonionic units $C_N$ can derive, of:
- hydroxyalkyl esters of α,β-ethylenically unsaturated acids, such as hydroxyethyl acrylate, hydroxyethyl methacrylate, hydroxypropyl acrylate, hydroxypropyl methacrylate, glycerol monomethacrylate, and the like,
- α,β-ethylenically unsaturated amides, such as acrylamide (AM), methacrylamide, N-methylolacrylamide, dimethylacrylamide, dimethylmethacrylamide, and the like,
- α,β-ethylenically unsaturated monomers carrying a water-soluble polyoxyalkylene segment of the polyethylene oxide type, such as, if appropriate random or block, polyethylene oxide and/or propylene oxide α-methacrylates (Bisomer S20W, S10W, and the like, from Laporte) or α,ω-dimethacrylates, Sipomer BEM from Rhodia (ω-behenyl polyoxyethylene methacrylate, optionally as a mixture), Sipomer SEM-25 from Rhodia (ω-tristyrylphenyl polyoxyethylene methacrylate), and the like,
- α,β-ethylenically unsaturated monomers which are precursors of hydrophilic units or segments, such as vinyl acetate, which, once polymerized, can be hydrolyzed to produce vinyl alcohol units or polyvinyl alcohol segments,
- vinylpyrrolidones,
- α,β-ethylenically unsaturated monomers of ureido type and in particular the methacrylamido of 2-imidazolidinone ethyl, optionally as a mixture (Sipomer WAM II from Rhodia),
- nonethylene glycol methyl ether acrylate or nonethylene glycol methyl ether methacrylate.

Mention may be made, as examples of anionic or potentially anionic monomers $C_A$ from which anionic or potentially anionic units $C_A$ can derive, of:
- monomers having at least one carboxyl functional group, such as α,β-ethylenically unsaturated carboxylic acids or the corresponding anhydrides, such as acrylic acid, acrylic anhydride, methacrylic acid, methacrylic anhydride, maleic acid, maleic anhydride, fumaric acid, itaconic acid, N-methacryloylalanine, N-acryloylglycine and their water-soluble salts,
- monomers which are precursors of carboxylate functional groups, such as tert-butyl acrylate, which produce, after polymerization, carboxyl functional groups by hydrolysis,
- monomers having at least one sulfate or sulfonate functional group, such as 2-sulfooxyethyl methacrylate, vinylbenzenesulfonic acid, allylsulfonic acid, 2-acrylamido-2-methylpropanesulfonic acid, sulfoethyl acrylate or methacrylate, sulfopropyl acrylate or methacrylate, and their water-soluble salts,
- monomers having at least one phosphonate or phosphate functional group, such as vinylphosphonic acid, and the like, ethylenically unsaturated phosphate esters, such as phosphates derived from hydroxyethyl methacrylate (Empicryl 6835 from RHODIA) and those derived from polyoxyalkylene methacrylates, and their water-soluble salts.

According to advantageous embodiments, the copolymer is:

A copolymer deriving from:
  A: SPE, preferably from 5 to 95 mol %, more preferably from 10 to 90 mol %, and
  B: MAPTAC, preferably from 5 to 95 mol %, more preferably from 10 to 90 mol %, a copolymer deriving from:
  A: SPE, preferably from 5 to 95 mol %, more preferably from 10 to 90 mol %, and
  B: DIQUAT, preferably from 5 to 95 mol %, more preferably from 10 to 90 mol %, a copolymer deriving from:
  A: SPE, preferably from 5 to 90 mol %, more preferably from 10 to 80 mol %,
  B: MAPTAC, preferably from 5 to 90 mol %, more preferably from 10 to 80 mol %, and C: acrylamide, preferably from 5 to 90 mol %, more preferably from 10 to 80 mol %,
a copolymer deriving from:
A: SPE, preferably from 5 to 90 mol %, more preferably from 10 to 80 mol %,
B: DIQUAT, preferably from 5 to 90 mol %, more preferably from 10 to 80 mol %, and
C: acrylamide, preferably from 5 to 90 mol %, more preferably from 10 to 80 mol %,
a copolymer deriving from:
A: SPP, preferably from 5 to 95 mol %, more preferably from 10 to 90 mol %, and
B: MAPTAC, preferably from 5 to 95 mol %, more preferably from 10 to 90 mol %,
a copolymer deriving from:
A: SPP, preferably from 5 to 95 mol %, more preferably from 10 to 90 mol %, and
B: DIQUAT, preferably from 5 to 95 mol %, more preferably from 10 to 90 mol %,
a copolymer deriving from:
A: SPP, preferably from 5 to 90 mol %, more preferably from 10 to 80 mol %,
B: MAPTAC, preferably from 5 to 90 mol %, more preferably from 10 to 80 mol %, and
C: acrylamide, preferably from 5 to 90 mol %, more preferably from 10 to 80 mol %, or
a copolymer deriving from:
A: SPP, preferably from 5 to 90 mol %, more preferably from 10 to 80 mol %,
B: DIQUAT, preferably from 5 to 90 mol %, more preferably from 10 to 80 mol %, and
C: acrylamide, preferably from 5 to 90 mol %, more preferably from 10 to 80 mol %.

The weight-average molar mass of the copolymer is preferably between 5000 g/mol and 400 000 g/mol (relative value, calibrated by aqueous GPC with polyethylene oxide standards). The absolute weight-average molar mass can preferably be between 10 000 and 4 000 000 g/mol.

The absolute weight-average molar mass is advantageously greater than or equal to 100 000 g/mol, preferably greater than or equal to 250 000 g/mol. The weight-average molar mass can in particular be less than or equal to 2 000 000 g/mol, or even 1 000 000 g/mol. Polymers of relatively high mass can improve the treatment of the surface, for example by greater deposition. In the context of radical polymerizations, which bring together the monomers and a free radical initiator, often in aqueous solution and at an appropriate temperature, the average molar mass can be controlled by the amount of initiator used: the less initiator used, the greater the average molar mass. Use may in particular be made of less than 1 mol %, indeed even less than 0.5 mol %, for example from 0.01 mol % to 0.25 mol %, with respect to the monomers involved, of initiator.

Preferably, the copolymer is water-soluble or water-dispersible.

The copolymer according to the invention can be presented in particular in the form of a powder, in the form of a dispersion in a liquid or in the form of a solution in a solvent (water or other). The form depends generally on the requirements related to the use for the copolymer. It can also be related to the process for the preparation of the copolymer.

Compositions

The copolymer can be used in a composition, typically a composition intended to be applied to a surface.

The copolymer can thus be, used in the fields of cosmetic compositions, compositions for domestic care purposes (detergency, laundry detergents, liquid dish soaps, dishwasher products, products for cleaning hard surfaces, and the like), compositions for industrial or institutional care purposes (in particular cleaning), compositions for the treatment of surfaces targeted at modifying the properties thereof, such as hydrophilicity or adhesion, compositions employed in techniques for the extraction of oil or gas, paint compositions, plant protection compositions, industrial or professional coatings or treatments intended to facilitate subsequent cleaning, or compositions for the treatment of metals or plastics.

In addition, the copolymer can be used as flocculating agent or agent for depositing on a surface or agent for helping in depositing on a surface.

Thus, useful compositions can be compositions for the treatment or modification of surfaces comprising:
a carrier, preferably a liquid carrier, for example a cosmetically acceptable carrier,
the copolymer,
optionally a surfactant,
optionally a salt, an acid and/or a base, and
optionally an agent for the treatment or modification of the surface.

The amount by weight of copolymer (as weight of dry matter), with respect to the composition, is preferably greater than 0.001%, preferably greater than 0.01%, for example of the order of 0.1 to 0.9%. It can be is less than 10%, often less than 5% and even less than 1%. The amount by weight can depend on a nature of the surface treatment or of the modification.

Advantageously, the composition comprises an anionic or amphoteric surfactant. The composition can comprise a nonionic surfactant. It can comprise a mixture or a combination of anionic, amphoteric and/or nonionic surfactants.

Advantageously, the units B are in the cationic form at the pH of the composition.

According to a preferred embodiment, the composition:
comprises an anionic or amphoteric surfactant, and
comprises coacervates or it forms coacervates by dilution and/or modification of the pH.

For this, the copolymer, the anionic or amphoteric surfactant, the carrier, optionally other surfactants, a salt, a base and/or acid, and their amounts, are such that at least a portion of system composed of the copolymer, of the anionic or amphoteric surfactant, of the carrier, and optionally the other surfactants, salt, base and/or acid,
forms coacervates by dilution and/or modification of the pH, or
comprises coacervates.

The agent for the treatment or modification of the surface can, for example, be a polyorganosiloxane, an antidandruff active principle, a fragrance, an oil or a UV screening agent.

As regards the composition, it can in particular be:
a cosmetic composition, preferably intended to be rinsed out, preferably a shampoo, a hair shaping product, a conditioner, a hair care product, a skincare product or a shower gel,
a detergent or rinsing composition for domestic or industrial or institutional care purposes, preferably for caring for the laundry or for cleaning or treating hard surfaces.

The composition can be used in the process for the treatment or modification of a surface comprising the following stages:
applying the composition to the surface, and
optionally removing the carrier or diluting the composition or modifying the pH.

When the surface is a skin or the hair, the treatment or the modification can, for example, be a conditioning of the skin or hair.

In the field of domestic, industrial or institutional care purposes, the surface can in particular be a textile surface (it being possible for the composition to be a laundry detergent or a softener, for example) or a hard surface.

The surface can also be a surface of nonwoven type, for example a surface present in domestic hygiene products, such as wipes, and/or a surface present in personal hygiene products, such as a textile surface used in the manufacture of diapers, of feminine protection products or of adult incontinence products.

Cosmetic Composition

When the copolymer is used in a cosmetic composition (or "formulation"), it can help in or contribute to deposition of material (conditioning effect) and/or, more generally, to optimizing cosmetic effects, such as softness, suppleness, disentangling, shine or suitability for styling on dry or wet hair. It can help in the design of formulations which are easy to prepare, easy to employ and satisfactorily stable.

In addition, it can contribute to providing novel cosmetic compositions, in particular intended to be rinsed out, exhibiting improved qualities as regards stability and/or simplification of the formulations and/or transparency and/or cosmetic qualities (mentioned above) and/or deposition of material (deposition of the copolymer or deposition of other materials, such as mineral, vegetable or synthetic oils, for example silicone oils or "polyorganosiloxanes").

The cosmetic compositions are preferably compositions intended to be rinsed out. They may, for example, be a shampoo, a shower gel or a conditioner. They may nevertheless be a hair care composition which is not intended to be rinsed out, for example a conditioner intended not to be rinsed out, a disentangling milk, an aqueous disentangling lotion, an aqueous smoothing lotion, a cuticle coating, a styling and/or restyling haircare product, an antisun product, a care cream, a makeup remover, a makeup, make-up-removing or moisturizing wipes, shaving foams or styling or fixing foams.

The invention also relates to the use of the copolymer in cosmetic compositions.

The compositions, when they comprise a conditioning agent, for example a silicone (equivalently known as a polyorganosiloxane), promote the deposition of said agent. The copolymer thus helps in the deposition of conditioning agents, more particularly silicones (or polyorganosiloxanes). In addition, the compositions comprising a polyorganosiloxane and the copolymer exhibit excellent conditioning properties, for the hair or the skin, and advantageous sensory or cosmetic properties which may be desired by consumers. Thus, they can provide an advantageous profile of softness, suppleness, body, disentangling, suitability for styling on wet hair and/or suitability for styling on dry hair. These effects can render the formulations simpler and/or less expensive. The compositions in addition exhibit satisfactory foaming properties, in particular in hard water.

The cosmetic compositions can advantageously comprise from 0.01% to 5% by weight of the copolymer, preferably from 0.05 to 1.5% by weight, for example from 0.1 to 0.5% by weight. It is specified that the copolymer can be introduced into the composition in the form of a more or less concentrated aqueous solution. The amounts mentioned above are amounts expressed on a dry basis.

Cosmetically Acceptable Carrier of the Cosmetic Compositions

Any cosmetically acceptable carrier which makes it possible to formulate the ampholyte copolymer and to obtain the cosmetic composition form desired for the targeted use can be used. Various carriers cosmetically acceptable for various types of formulation are known to a person skilled in the art.

Mention may be made, as examples of cosmetically acceptable carriers, of aqueous carriers (comprising water), alcoholic carriers (comprising an alcohol, for example ethanol, isopropanol, ethylene glycol, propylene glycol or polyethylene glycols) or aqueous/alcoholic carriers (comprising a mixture of water and of an alcohol, for example ethanol, isopropanol, ethylene glycol or polyethylene glycols). Certain volatile or nonvolatile oils can also be used. Mention is made, for example, of fluid silicones, such as cyclopentasiloxane, for example Mirasil CM5, sold by Rhodia.

A person skilled in the art knows to choose the carriers suited to the types of formulation desired and to the uses targeted. For example, aqueous carriers are generally used for shampoos or shower gels. A propylene glycol carrier can be used for compositions in the form of creams. A cyclomethicone carrier can be used for makeup compositions, for example for foundations.

Surfactants in the Cosmetic Compositions

The composition is an aqueous composition optionally comprising surfactants. A mixture of different surfactants may be involved. The surfactants included in the composition preferably comprise at least one anionic surfactant. The surfactants can also comprise amphoteric (true amphoteric or zwitterionic) surfactants, neutral surfactants (nonionic surfactants) and/or cationic surfactants. The compositions comprising at least one anionic surfactant and at least one amphoteric surfactant are particularly advantageous, in particular for reasons of softness. The total content of surfactants in the composition is generally between 0 and 30% by weight.

For compositions intended for the treatment of the hair, such as shampoos, the content of surfactant is advantageously between 10 and 20% by weight. Such compositions can comprise salts, for example sodium chloride or ammonium chloride, advantageously in a content of less than 3% by weight.

For compositions intended for the treatment of the skin, such as shower gels, the content of surfactant is advantageously between 5 and 15% by weight. Such compositions also preferably comprise at least 2% by weight of salts, for example sodium chloride or ammonium chloride.

For conditioners, the content of surfactants can be less than 5% by weight.

The proportion by weight of anionic surfactants, with respect to the combined surfactants, is preferably greater than 50%, preferably greater than 70%.

Parameters (pH) of Use for the Cosmetic Compositions

The pH of the composition can be is greater than or equal to 5.5. It is, for example, between 5.5 and 7.5, preferably between 6 and 6.5. However, the pH of the composition can be from 3.5 to less than 5.5, preferably between 4.5 and less than 5.5, preferably from 5 to less than 5.5. The pH obviously depends on the compounds present in the composition. It is obviously possible to use, in the composition, pH-regulating agents, which are acids or bases, for example citric acid or sodium hydroxide, potassium hydroxide or ammonium hydroxide.

Natures of the Surfactants for the Cosmetic Compositions

The anionic surfactants can be chosen from the following surfactants:

alkyl ester sulfonates, for example of formula R—CH($SO_3M$)-$CH_2COOR'$, or alkyl ester sulfates, for example of formula R—CH($OSO_3M$)-$CH_2COOR'$, where R represents a $C_8$-$C_{20}$, preferably $C_{10}$-$C_{16}$, alkyl radical, R' represents a $C_1$-$C_6$, preferably $C_1$-$C_3$, alkyl radical and M represents an alkaline earth metal cation, for example sodium, or the ammonium cation. Mention may very particularly be made of methyl ester sulfonates in which the radical R is a $C_{14}$-$C_{16}$ radical;

alkylbenzenesulfonates, more particularly $C_9$-$C_{20}$ alkylbenzenesulfonates, primary or secondary alkylsulfonates, in particular $C_8$-$C_{22}$ alkylsulfonates, or alkylglycerolsulfonates;

alkyl sulfates, for example of formula $ROSO_3M$, where R represents a $C_{10}$-$C_{24}$, preferably $C_{12}$-$C_{20}$, alkyl or hydroxyalkyl radical and M represents a cation with the same definition as above;

alkyl ether sulfates, for example of formula $RO(OA)_nSO_3M$, where R represents a $C_{10}$-$C_{24}$ preferably $C_{12}$-$C_{20}$, alkyl or hydroxyalkyl radical, OA represents an ethoxylated and/or propoxylated group; M represents a cation with the same definition as above and n varies generally from 1 to 4, such as, for example, lauryl ether sulfate with n=2;

alkylamide sulfates, for example of formula $RCONHR'OSO_3M$, where R represents a $C_2$-$C_{22}$, preferably $C_6$-$C_{20}$, alkyl radical, R' represents a $C_2$-$C_3$ alkyl radical and M represents a cation with the same definition as above, and their polyalkoxylated (ethoxylated and/or propoxylated) derivatives (alkylamido ether sulfates);

salts of saturated or unsaturated fatty acids, for example such as $C_8$-$C_{24}$, preferably $C_{14}$-$C_{20}$, fatty acids, and of an alkaline earth metal cation, N-acyl-N-alkyltaurates, alkylsethionates, alkyl-succinamates and alkylsulfosuccinates, monoesters or diesters of sulfosuccinates, N-acylsarcosinates or polyethoxycarboxylates;

phosphate mono- and diesters, for example of the following formula:

$(RO)_x$—$P(=O)$ $(OM)_{x'}$, where R represents an optionally polyalkoxylated alkyl, alkylaryl, arylalkyl or aryl radical, x and x' are equal to 1 or 2, provided that the sum of x and x' is equal to 3, and M represents an alkaline earth metal cation.

The nonionic surfactants can be chosen from the following surfactants:
alkoxylated fatty alcohols;
alkoxylated triglycerides;
alkoxylated fatty acids;
alkoxylated sorbitan esters;
alkoxylated fatty amines;
alkoxylated di(1-phenylethyl)phenols;
alkoxylated tri(1-phenylethyl)phenols;
alkoxylated alkylphenols;
the products resulting from the condensation of ethylene oxide with a hydrophobic compound resulting from the condensation of propylene oxide with propylene glycol, such as the Pluronic products sold by BASF;
the products resulting from the condensation of ethylene oxide with the compound resulting from the condensation of propylene oxide with ethylene-diamine, such as the Tetronic products sold by BASF;
alkylpolyglycosides, such as those described in U.S. Pat. No. 4,565,647;
fatty acid amides, for example $C_8$-$C_{20}$ fatty acid amides.

The amphoteric surfactants (true amphoteric, comprising an ionic group and a potentially ionic group of opposite charge, or zwitterionic, simultaneously comprising two opposite charges) can be chosen from the following surfactants:
betaines generally, in particular carboxybetaines, for example lauryl betaine (Mirataine BB from Rhodia) or octyl betaine, or amidoalkyl betaines, such as cocamidopropyl betaine (CAPB) (Mirataine BDJ from Rhodia Chimie);
sulfobetaines or sultaines, such as cocamidopropyl hydroxysultaine (Mirataine CBS from Rhodia);
alkylamphoacetates and alkylamphodiacetates, such as, for example, comprising a coco or lauryl chain (Miranol C2M, C32 and L32 in particular from Rhodia);
alkylamphopropionates or alkylamphodipropionates (Miranol C2M SF);
alkyl amphohydroxypropyl sultaines (Miranol CS).

The cationic surfactants can be chosen from salts of optionally polyethoxylated primary, secondary or tertiary fatty amines, quaternary ammonium salts, such as tetraalkylammonium, alkylamidoalkylammonium, trialkylbenzylammonium, trialkylhydroxyalkylammonium or alkylpyridinium chlorides or bromides, imidazoline derivatives or amine oxides having a cationic nature.

Mention may be made, as examples of useful compositions, of:

"Sodium" compositions for shampoos typically comprising 12 to 16% by weight of sodium alkyl ether sulfate (for example, sodium lauryl ether sulfate "SLES") or of a mixture of sodium alkyl ether sulfate and of sodium alkyl sulfate (for example, sodium lauryl sulfate "SLS"), 1 to 3% of an amphoteric surfactant (for example, cocamidopropyl betaine "CAPB") and 0.5 to 2% of a salt (for example, sodium chloride).

"Ammonium" compositions for shampoos typically comprising 12 to 16% by weight of ammonium alkyl ether sulfate (for example, ammonium lauryl ether sulfate "ALES") or of a mixture of ammonium alkyl ether sulfate and of ammonium alkyl sulfate (for example, ammonium lauryl sulfate "ALS"), 1 to 3% of an amphoteric surfactant (for example, cocamidopropyl betaine "CAPB") and 0 to 2% of a salt (for example, ammonium chloride).

"Sodium" compositions for shower gels typically comprising 6 to 10% by weight of sodium alkyl ether sulfate (for example, sodium lauryl ether sulfate "SLES") or of a mixture of sodium alkyl ether sulfate and of sodium alkyl sulfate (for example, sodium lauryl sulfate "SLS"), 1 to 3% of an amphoteric surfactant (for example, cocamidopropyl betaine "CAPB") and 2 to 4% of a salt (for example, sodium chloride).

"Ammonium" compositions for shower gels typically comprising 6 to 10% by weight of ammonium alkyl ether sulfate (for example, ammonium lauryl ether sulfate "ALES") or of a mixture of ammonium alkyl ether sulfate and of ammonium alkyl sulfate (for example, ammonium lauryl sulfate "ALS"), 1 to 3% of an amphoteric surfactant (for example, cocamidopropyl betaine "CAPB") and 0 to 4% of a salt (for example, ammonium chloride).

Other Compounds which can be Present in the Cosmetic Compositions

The composition can comprise any other compound used in cosmetic compositions intended to be rinsed out (shampoo, shower gel, conditioner, and the like) or intended not to be rinsed out.

Mention is made, for example, of sequestering agents, softening agents, foam modifiers, colorants, pearlescent agents (pearlizers), moisturizing agents, antidandruff or antiseborrheic agents, suspending agents, emulsifying agents, ceramides, pseudoceramides, electrolytes, fatty acids, fatty acid esters, hydroxy acids, thickening agents, fragrances, preservatives, organic or inorganic sunscreens, proteins, vitamins, polymers, silicones (polyorganosiloxanes), or stabilizing and/or conditioning agents and/or conditioning aid, other than the ampholyte copolymer and than the polyorganosiloxanes, in particular polymers. Some of these compounds are described in detail below.

Stabilizing and/or Conditioning Agent and/or Conditioning Aid

The cosmetic composition according to the invention can advantageously comprise at least one stabilizing and/or conditioning agent and/or conditioning aid. The term "suspending agents" is also sometimes used. The term "conditioning aid" is understood to mean that the presence of the agent improves the conditioning related to other compounds, for example oils or silicones. These agents are understood as agents other than the polyorganosiloxane of formula (I). Such agents are known to a person skilled in the art. The composition according to the invention can comprise several of these agents (mixtures or combinations), in order to combine their effects and/or to create synergies. Furthermore, some agents can play several roles. This is the case, for example, of polysaccharides and their cationic derivatives, for example cationic guar derivatives.

The proportion by weight of such agents can be typically from 0.1% to 10% by weight, preferably from 0.3% to 8% by weight, for polysaccharides or other agents.

Mention may be made, as examples of stabilizing agents which are particularly useful for compositions comprising polyorganosiloxanes, of:

crosslinked polyacrylates, for example polymers of Carbopol or Carbomer type sold by BF Goodrich or Noveon, Acritamer sold by Rita or Tego Carbomer sold by Goldschmidt. These compounds can typically be present in an amount of 0.1 to 3% by weight, preferably of 0.3 to 2% by weight, with respect to the composition;

$C_{10}$-$C_{30}$ alkyl PEG 20 acrylate/amino-acrylate/itaconate copolymers sold by National Starch under the name Structure Plus. These compounds can typically be present in an amount of 0.1 to 3% by weight, preferably of 0.3 to 2% by weight, with respect to the composition;

insoluble solids forming a network in the composition. They can be ethylene glycol mono- and/or diesters of fatty acids, the fatty acids preferably being $C_{16}$-$C_{18}$ fatty acids. The solid can in particular be ethylene glycol distearate (EGDS), for example sold by Rhodia as a concentrate with other ingredients under the name Mirasheen. This compound can typically be present in an amount of 3 to 10% by weight, preferably of 5 to 8% by weight, with respect to the composition.

Mention may also be made of viscosifying, gelling or texturing agents, such as the anionic acrylic copolymers of Aculyne type sold by ISP or Röhm & Haas), or polysaccharides and their noncationic derivatives, such as cellulose derivatives, for example hydroxypropylcellulose or carboxymethylcellulose, nonionic guar derivatives, such as hydroxypropyl guar (for example, the Jaguar HP product sold by Rhodia), locust bean gum, tara gum or cassia gum, xanthan gum (for example, the Rhodicare product sold by Rhodia), succinoglycans (for example, Rheozan sold by Rhodia), alginates, carrageenans, chitin derivatives or any other polysaccharide having a texturing role. These polysaccharides and their derivatives can be incorporated alone or in synergistic combination with other polysaccharides. These compounds can typically be present in an amount of 0.1 to 3% by weight, preferably of 0.3 to 1% by weight, with respect to the composition.

Mention may be made, as examples of stabilizing agents and/or of conditioning agents and/or of conditioning aids, of:

cationic polymers derived from polysaccharides, for example cationic cellulose derivatives, cationic starch derivatives, cationic guar derivatives or cationic locust bean derivatives;

synthetic cationic polymers;

mixtures or combinations of these agents.

The synthetic or nonsynthetic cationic polymers which can act as conditioning agent are in particular polymers of polyquaternium type, such as, for example, polyquaternium-1, polyquaternium-2, polyquaternium-4, polyquaternium-5, polyquaternium-6 (also known as Merquat 1000, available from Nalco), polyquaternium-7 (also known as Merquat 5500, available from Nalco), polyquaternium-8, polyquaternium-9, polyquaternium-10 (also known as Polymer JR 400, sold by Amercol), polyquaternium-11, polyquaternium-12, polyquaternium-13, polyquaternium-14, polyquaternium-15, polyquaternium-16, polyquaternium-17, polyquaternium-18, polyquaternium-19, polyquaternium-20, polyquaternium-22 (also known as Merquat 280, Merquat 281 or Merquat 298, available from Nalco), polyquaternium-24, polyquaternium-27, polyquaternium-28, polyquaternium-29 (also known as Kytamer KCO, available from Amerchol), polyquaternium-30, polyquaternium-31, polyquaternium-32, polyquaternium-33, polyquaternium-34, polyquaternium-35, polyquaternium-36, polyquaternium-37, polyquaternium-39 (also known as Merquat 3300 or Merquat 3331, available from Nalco), polyquaternium-44, polyquaternium-27 (also known as Merquat 2001, available from Nalco) and polyquaternium-55.

As mentioned above, the composition can comprise other polymers, synthetic or natural or resulting from biological preparation processes, if appropriate functionalized, for example by cationic or neutral groups. These polymers can have a stabilizing or structuring effect on the compositions and/or a conditioning effect (deposition at the surface of the skin or hair).

Mention is made, as examples, of cationic polysaccharide derivatives, such as guar or cellulose derivatives. Cationic polymers functionalized by hydrophobic groups, such as $C_1$-$C_{14}$, preferably $C_2$-$C_8$, alkyl chains, optionally exhibiting a hydroxyl group, can be used. These hydrophobic groups are attached to the main polymer chain via ether bonds.

Furthermore, in the case of hydrophobically or non-hydrophobically modified cationic guars, the cationic group is a quaternary ammonium group carrying three identical or different radicals chosen from hydrogen or an alkyl radical comprising from 1 to 22 carbon atoms, more particularly from 1 to 14 carbon atoms and advantageously from 1 to 3 carbon atoms. The counterion is a halogen, preferably chlorine.

In the case of hydrophobically or nonhydrophobically modified cationic celluloses, the cationic group is a quaternary ammonium group carrying three identical or different radicals chosen from hydrogen or an alkyl radical comprising from 1 to 10 carbon atoms, more particularly from 1 to 6 carbon atoms and advantageously from 1 to 3 carbon atoms. The counterion is a halogen, preferably chlorine.

Mention may be made, among cationic guar derivatives, of guar hydroxypropyltrimonium chloride (Jaguar C13S, Jaguar C14S, Jaguar C17, Jaguar Excel or Jaguar C 2000, sold by Rhodia Chimie) or hydroxypropyl guar hydroxypropyltrimonium chloride (Jaguar C162, sold by Rhodia).

Use can be made, among cationic cellulose derivatives, of cellulose [2-hydroxy-3-{trimethylammonio}propyl]-poly(oxy-1,2-ethanediyl)ether chloride or polyquaternium-10, such as Polymer JR400 (INPI name: PQ10), sold by Amerchol.

Nonionic polysaccharide derivatives, for example hydroxypropyl guar, can also be used.

Synthetic polymers, more particularly homopolymers, such as polymethacrylamidopropyl trimonium chloride (Polycare 133, sold by Rhodia Chimie), may likewise be suitable.

The cationic polymers more particularly exhibit a weight-average molar mass of at least 2000 g/mol and more preferably of between $2\times10^4$ and $3\times10^6$ g/mol, according to their degree of polymerization possible. The weight-average molar masses of the polymers are usually measured by size exclusion. They can optionally be measured directly by light scattering or from the intrinsic viscosity using calibration according to "Viscosity-Molecular weight relationship, intrinsic chain flexibility and dynamic solution properties of guar galactomannan" by G. Robinson, S. B. Ross Murphy and E. R. Morris, Carbohydrate Research, 107, pp 17-32, 1982.

In the case of cationic polysaccharide derivatives, the degree of hydroxyalkylation (molar substitution or MS) is preferably between 0 and 1.2. However, in the case of these polymers, the degree of cationicity (degree of substitution or DS) is more particularly between 0.01 and 0.6. This is the case, for example, of Jaguar C162 and Jaguar C2000, sold by Rhodia Chimie.

Polyorganosiloxanes (Silicones)

The composition can comprise a silicone (silicone oil). The term "silicone" or "polyorganosiloxane" is understood to mean any organosiloxane compound comprising alkyl (for example methyl) groups and/or functionalized by groups other than alkyl groups.

The polyorganosiloxane is advantageously (in shampoos and conditioners in particular) a nonvolatile and water-insoluble polyorganosiloxane. It advantageously exhibits a viscosity of between 1000 and 2 000 000 mPa·s, preferably between 5000 and 500 000 mPa·s. The polyorganosiloxane can in particular be a polydimethylorganosiloxane ("PDMS", INCI name: dimethicone), or a polyorganosiloxane exhibiting amine groups (for example, amodimethicone according to the INCI name), quaternary ammonium groups (for example, silicone quaternium-1 to −10 according to the INCI name), hydroxyl groups (terminal or nonterminal), polyoxyalkylene groups, for example polyethylene oxide and/or polypropylene oxide groups (as terminal groups, as blocks within a PDMS chain or as grafts), or several of these groups.

The amount of polyorganosiloxane present in the composition can typically be from 0.1% to 5% by weight, for example from 0.5% to 1.5% or 2% by weight.

The polyorganosiloxane (silicone) is preferably present in the composition in the emulsion form (liquid silicone droplets dispersed in the aqueous phase). The emulsion can in particular be an emulsion for which the mean size of the droplets is greater than or equal to 2 µm and/or for which the mean size of the droplets is greater than or between 0.15 µm and 2 µm or for which the mean size of the droplets is less than or equal to 0.15 µm.

The droplets of the emulsion can be more or less large in size. Reference may thus be made to microemulsions, to miniemulsions or to macroemulsions. In the present patent application, the term "emulsion" covers in particular all these types of emulsion. Without wishing to be committed to any one theory, it is specified that microemulsions are generally thermodynamically stable systems generally comprising large amounts of emulsifying agents. The other emulsions are generally systems in the non-thermodynamically stable state which retain for a certain time, in the metastable state, the mechanical energy provided during the emulsification. These systems generally comprise lesser amounts of emulsifying agents.

The emulsions can be obtained by mixing the carrier, preferably aqueous carrier, the polyorganosiloxane and generally an emulsifying agent, and then emulsifying. It is possible to speak of in situ emulsification.

The compositions in the emulsion form can also be obtained by mixing the carrier, preferably aqueous carrier, with a preprepared emulsion of droplets comprising the polyorganosiloxane in an external phase which is preferably miscible with the cosmetically acceptable carrier, preferably of the same nature as said carrier, preferably an aqueous carrier. This embodiment may be preferred as it is simple to implement. In addition, this embodiment is particularly suitable for the implementation of cosmetic compositions in which the polyorganosiloxane is in the microemulsion form. It is possible to speak of preemulsification.

According to a specific embodiment, the emulsion is a microemulsion, the size of the droplets of which is less than 0.15 µm. In this embodiment, the composition preferably comprises a proportion of emulsifying agent of greater than 10% by weight, preferably at least 15% by weight, with respect to the weight of polyorganosiloxane.

The size of the microemulsion droplets can be measured on an emulsion prepared prior to this introduction into the cosmetic composition by dynamic light scattering (QELS), for example as described below. The equipment used is, for example, composed of a Spectra-Physics 2020 laser, of a Brookhaven 2030 correlator and of the associated computing. As the sample is concentrated, it is diluted in deionized water and filtered through a 0.22 µm filter in order, at the end, to be at 2% by weight. The diameter obtained is an apparent diameter. The measurements are carried out at angles of 90° and 135°. For the size measurements, in addition to the conventional analysis by cumulants, the autocorrelation function is run in three ways (the exponential sampling or EXPSAM described by Pr. Pike, the "Non Negatively Constrained Least Squares" or NNLS method and the CONTIN method described by Pr. Provencher) which each give a size distribution weighted by the scattered intensity and not by the weight or the number. The refractive index and the viscosity of the water are taken into account.

According to an advantageous form, the microemulsion is transparent. The microemulsion can, for example, exhibit a transmittance of at least 90%, preferably of at least 95%, at a wavelength of 600 nm, measured, for example, using a Lambda 40 UV-Vis spectrometer at a concentration of 0.5% by weight in water. In this context, the cosmetic composition can advantageously be transparent. It can, for example, exhibit a transmittance of at least 90%, preferably of at least 95%, at a wavelength of 600 nm, measured, for example, using a Lambda 40 UV-Vis spectrometer.

According to another specific embodiment, the emulsion is an emulsion for which the mean size of the droplets is greater than or equal to 0.15 µm, for example greater than 0.5 µm, or than 1 µm, or than 2 µm, or than 10 µm, or than 20 µm, and preferably less than 100 µm. The size of the droplets can be measured, by optical microscopy and/or laser particle sizing (Horiba LA-910 laser scattering analyzer), on an emulsion prepared prior to its introduction into the cosmetic composition or directly on the cosmetic composition diluted in water. In this embodiment, the composition preferably comprises a proportion of emulsifying agent of less than 10% by weight, with respect to the weight of polyorganosiloxane.

Emulsifying agents of use in the preparation of polyorganosiloxane emulsions are in particular nonionic surfactants, preferably polyalkoxylated surfactants, for example chosen from alkoxylated fatty alcohols, alkoxylated triglycerides, alkoxylated fatty alcohols, alkoxylated sorbitan esters, alkoxylated fatty amines, alkoxylated di(1-phenylethyl)phenols, alkoxylated tri(1-phenylethyl)phenols and alkoxylated alkylphenols, where the number of alkoxy units, more particularly oxyethylene and/or oxypropylene units, is such that the HLB value is greater than or equal to 10.

Mention may be made, among the silicone derivatives which are soluble in the water of the composition, inter alia, of dimethicone copolyols (Mirasil DMCO, sold by Rhodia Chimie).

As relates to the silicones which are provided in the form of dispersions which are insoluble in the water of the composition, use may suitably be made of water-insoluble and nonvolatile organopolysiloxanes, among which may be mentioned polyalkylsiloxane, polyarylsiloxane or polyalkylarylsiloxane oils, gums or resins or their water-insoluble functionalized derivatives, or their mixtures, which are nonvolatile.

Said organopolyosiloxanes are regarded as water-insoluble and nonvolatile if their solubility in water is less than 50 g/liter and their intrinsic viscosity is at least 3000 mPa·s at 25° C.

Mention may be made, as examples of water-insoluble and nonvolatile organopolysiloxanes or silicones, of silicone gums, such as, for example, the diphenyl dimethicone gum sold by Rhodia Chimie, and preferably the polydimethylsiloxanes exhibiting a viscosity at least equal to $6 \times 10^5$ mPa·s at 25° C. and more preferably still those with a viscosity of greater than $2 \times 10^6$ mPa·s at 25° C., such as Mirasil DM 500 000®, sold by Rhodia Chimie.

According to the invention, the water-insoluble and nonvolatile organopolysiloxane or silicone occurs in a form dispersed within the cosmetic composition including it.

The water-insoluble and nonvolatile organopolysiloxane or silicone exists in the form of particles or droplets, the size of which can be chosen according to the nature of the cosmetic composition or the performance desired for said composition. Generally, this size can vary from 0.01 to 70 microns.

Preferably, this size is of the order of 0.1 to 50 microns, very particularly of the order of 1 to 30 microns.

In order to facilitate the use thereof, these organopolysiloxanes can be dispersed or dissolved beforehand in volatile or nonvolatile silicone derivatives of low viscosity and then emulsified in the cosmetic composition.

Mention may be made, among these silicones of low viscosity, of volatile cyclic silicones and polydimethylsiloxanes of low weight.

Use can also be made of functionalized silicone derivatives, such as aminated derivatives, directly in the form of emulsions or starting from a preformed microemulsion. They can be compounds known under the term of aminated silicones or hydroxylated silicones. Mention is made of Mirasil ADM-E (amodimethicone), sold by Rhodia, and dimethiconol.

Mention is in particular made, as polyorganosiloxanes which can be used, of:
  polyorganosiloxanes comprising —Si(CH$_3$)$_2$O— units and —SiY(CH$_3$)O— units where Y is a —(CH$_2$)$_3$—NH(CH$_2$)$_2$—NH$_2$ or —(CH$_2$)$_3$—NH$_2$ group,
  polyorganosiloxanes comprising —Si(CH$_3$)$_2$O— units and HO—Si(CH$_3$)$_2$O— terminal units and/or —Si(CH$_3$)(OH)O— nonterminal units,
  polyorganosiloxanes comprising —Si(CH$_3$)$_2$O— units and —SiY(CH$_3$)O— units where Y is -L$^X$-Z$^X$-Palc where L$^X$ is a divalent connecting group, preferably an alkylene group, Z$^X$ is a covalent bond or a divalent joining group comprising a heteroatom, Palc is a group of formula [OE]$_s$-[OP]$_t$—X', in which OE is a group of formula —CH$_2$—CH$_2$—O—, OP is a group of formula —CH$_2$—CHCH$_3$—O— or —CHCH$_3$—CH$_2$—O—, X' is a hydrogen atom or a hydrocarbon group, s is a mean number greater than 1 and t is a mean number greater than or equal to 0,
  polyorganosiloxanes, the chain of which comprises at least one block comprising units of formula —Si(CH$_3$)$_2$O— units and at least one —[OE]$_s$-[OP]$_t$— block,
  polyorganosiloxanes comprising —Si(CH$_3$)$_2$O— units and/or —Si(CH$_3$)RO— and/or —SiR$_2$O— and/or R—Si(CH$_3$)$_2$O— and/or H$_3$C—SiR$_2$O— and/or R—SiR$_2$O— units, where R, which can be identical or different, is an alkyl group other than a methyl group, an aryl group, an alkylaryl group or an aralkyl group.

Other Compounds

It is likewise possible to envisage using oils which may perform conditioning, protective or emollient roles. Such oils are generally chosen from alkyl monoglycerides, alkyl diglycerides, triglycerides, such as oils extracted from plants (palm oil, coconut oil, cottonseed oil, soybean oil, sunflower oil, olive oil, grape seed oil, sesame oil, peanut oil, castor oil, and the like) or oils of animal origin (tallow, fish oils and the like), derivatives of these oils, such as hydrogenated oils, lanolin derivatives, petrolatum, mineral oils or liquid paraffins, perhydrosqualane, squalene, diols, such as 1,2-dodecanediol, cetyl alcohol, stearyl alcohol, oleyl alcohol, fatty esters, such as isopropyl palmitate, 2-ethylhexyl cocoate or myristyl myristate, lactic acid esters, stearic acid, behenic acid or isostearic acid.

It is also possible to incorporate bactericidal or fungicidal agents in the cosmetic composition, in the form of dispersions or solutions, in order to improve the disinfecting of the skin, such as, for example, triclosan, antidandruff agents, such as, in particular, zinc pyrithione or octopyrox, or insecticidal agents, such as natural or synthetic pyrethroids.

The cosmetic compositions can also comprise agents for protecting the skin and/or hair against attacks from the sun and UV radiation. Thus, the compositions can comprise sunscreens, which are chemical compounds which strongly absorb UV radiation, such as the compounds authorized in European Directive No. 76/768/EEC, its appendices and the subsequent amendments to this directive.

In the case where the various constituent components of the cosmetic composition exhibit an excessively low solubility in the composition or when they exist in the solid form at ambient temperature, said constituent components can advantageously be dissolved in an organic vehicle, such as mineral or natural oils, silicone derivatives or waxes, or alternatively can be encapsulated in matrices, such as polymers of latex type.

The cosmetic compositions forming the subject matter of the invention can also comprise fixative resins.

These fixative resins, when they are present, are generally present at concentrations of between 0.01 and 10%, preferably between 0.5 and 5%.

The fixative resins participating in the cosmetic compositions are chosen more particularly from the following resins:
  methyl acrylate/acrylamide copolymers, poly(vinyl methyl ether/maleic anhydride) copolymers, vinyl acetate/crotonic acid copolymers, octyl-acrylamide/methyl acrylate/butylaminoethyl methacrylate copolymers, polyvinylpyrrolidones, polyvinyl-pyrrolidone/methyl methacrylate copolymers, polyvinylpyrrolidone/vinyl acetate copolymers, polyvinyl alcohols, poly(vinyl alcohol/crotonic acid) copolymers, poly(vinyl/alcohol/maleic anhydride) copolymers, hydroxypropyl celluloses, hydroxypropyl guars, sodium polystyrenesulfonates, polyvinyl-pyrrolidone/ethyl methacrylate/methacrylic acid terpolymers, poly (methyl vinyl ether/maleic acid) monomethyl ethers or polyvinyl acetates grafted to polyoxyethylene backbones (EP-A-219 048), copolyesters derived from terephthalic and/or isophthalic and/or sulfoisophthalic acid, anhydride or a diester thereof and from a diol, such as:
  polyester copolymers based on ethylene terephthalate and/or propylene terephthalate and polyoxyethylene terephthalate units (U.S. Pat. No. 3,959,230, U.S. Pat. No. 3,893,929, U.S. Pat. No. 4,116,896, U.S. Pat. No. 4,702,857, U.S. Pat. No. 4,770,666);
  sulfonated polyester oligomers obtained by sulfonation of an oligomer derived from ethoxylated allyl alcohol, from dimethyl terephthalate and from 1,2-propanediol (U.S. Pat. No. 4,968,451);
  polyester copolymers derived from dimethyl terephthalate, from isophthalic acid, from dimethyl sulfoisophthalate and from ethylene glycol (EP-A-540 374);
  copolymers comprising polyester units derived from dimethyl terephthalate, from isophthalic acid, from dimethyl sulfoisophthalate and from ethylene glycol and polyorganosiloxane units (FR-A-2 728 915);
  sulfonated polyester oligomers obtained by condensation of isophthalic acid, of dimethyl sulfosuccinate and of diethylene glycol (FR-A-2 236 926);
  polyester copolymers based on propylene terephthalate and polyoxyethylene terephthalate units and terminated by ethyl or methyl units (U.S. Pat. No. 4,711,730) or polyester oligomers terminated by alkylpolyethoxy groups (U.S. Pat. No. 4,702,857) or anionic sulfopolyethoxy (U.S. Pat. No. 4,721,580) or sulfoaroyl (U.S. Pat. No. 4,877,896) groups;
  polyester-polyurethanes obtained by reaction of a polyester, obtained from adipic acid and/or from terephthalic acid and/or from sulfoisophthalic acid and from a diol, with a prepolymer comprising isocyanate terminal groups obtained from a polyoxyethylene glycol and from a diisocyanate (FR-A-2 334 698);
ethoxylated monoamines or polyamines, polymers of ethoxylated amines (U.S. Pat. No. 4,597,898, EP-A-11 984).

Preferably, the fixative resins are chosen from polyvinylpyrrolidones (PVP), copolymers of vinylpyrrolidone and of methyl methacrylate, copolymers of vinylpyrrolidone and of vinyl acetate (VA), poly(ethylene glycol terephthalate/ethylene glycol) copolymers, poly(ethylene glycol terephthalate/ethylene glycol/sodium sulfoisophthalate) copolymers, and their blends.

These fixative resins are preferably dispersed or dissolved in the chosen vehicle.

The cosmetic compositions forming the subject matter of the invention can also comprise polymeric derivatives performing a protective role.

These polymeric derivatives can be present in amounts of the order of 0.01-10% by weight, preferably approximately 0.1-5% by weight, and very particularly of the order of 0.2-3% by weight.

These agents can in particular be chosen from:
  nonionic cellulose derivatives, such as cellulose hydroxyethers, methylcellulose, ethylcellulose, hydroxypropyl methylcellulose or hydroxybutyl methylcellulose;
  polyvinyl esters grafted to polyalkylene backbones, such as polyvinyl acetates grafted to polyoxyethylene backbones (EP-A-219 048);
  polyvinyl alcohols.

The cosmetic compositions forming the subject matter of the invention can also comprise plasticizers.

Said plasticizers, if they are present, can represent between 0.1 and 20% of the formulation, preferably from 1 to 15%.

Mention may be made, among particularly useful plasticizers, of adipates, phthalates, isophthalates, azelates, stearates, silicone copolyols, glycols, caster oil or their mixtures.

It is also advantageously possible to add metal-sequestering agents to these compositions, more particularly those which sequester calcium, such as citrate ions.

It is also possible to incorporate humectants in the cosmetic compositions forming the subject matter of the invention, which humectants include, inter alia, glycerol, sorbitol, urea, collagen, gelatin, aloe vera, hyaluronic acid or water-soluble volatile solvents, such as ethanol or propylene glycol, the contents of which can reach up to 60% by weight of the composition.

In order to further reduce irritation of or attack on the scalp, it is also possible to add water-soluble or water-dispersible polymers, such as collagen or some non-allergizing derivatives of animal or plant proteins (wheat protein hydrolysates, for example), natural hydrocolloids (guar gum, locust bean gum, tara gum, and the like) or hydrocolloids resulting from fermentation processes, and derivatives of these polycarbohydrates, such as nonionic modified celluloses, such as, for example, hydroxyethylcellulose, or anionic modified celluloses, such as carboxymethylcellulose, or guar or locust bean derivatives, such as their nonionic derivatives (for example, hydroxypropyl guar) or the anionic derivatives (carboxymethyl guar and carboxymethyl hydroxypropyl guar).

Inorganic powders or particles, such as calcium carbonate, sodium bicarbonate, calcium dihydrogenphosphate, inorganic oxides in the powder form or in the colloidal form (particles with a size of less than or of the order of a micrometer, sometimes of a few tens of nanometers), such as titanium dioxide or silica, aluminum salts, generally used as antiperspirants, kaolin, talc, clays and their derivatives, and the like, can be added to these compounds in combination.

Preservatives, such as the methyl, ethyl, propyl and butyl esters or p-hydroxybenzoic acid, sodium benzoate, Germaben® or any chemical agent which prevents proliferation of bacteria or molds and which is conventionally used in cosmetic compositions, can also be introduced into the aqueous cosmetic compositions according to the invention, generally at a level of 0.01 to 3% by weight.

The amount of these products is usually adjusted in order to prevent any proliferation of bacteria, molds or yeasts in the cosmetic compositions.

Alternatively to these chemical agents, it is sometimes possible to use agents which modify the activity of the water and which greatly increase the osmotic pressure, such as carbohydrates or salts.

In order to protect the skin and/or hair from attacks from the sun and UV radiation, it is possible to add organic or inorganic sunscreens to the compositions, for example inorganic particles, such as zinc oxide, titanium dioxide or cerium oxides, in the powder form or in the form of colloidal particles, alone or as a mixture. These powders can optionally be surface treated in order to enhance the effectiveness of their UV protective effect or in order to facilitate their incorporation in the cosmetic formulations or in order to inhibit surface photoreactivity. The organic sunscreens can in particular be introduced into the polyorganosiloxane, if it is present in the composition.

If necessary, and with the aim of enhancing the comfort during use of the composition by the consumer, it is possible to add, to these ingredients, one or more fragrances, coloring agents, among which may be mentioned the products described in Appendix IV ("List of colouring agents allowed for use in cosmetic products") of the European Directive No. 76/768/EEC of 27 Jul. 1976, known as the Cosmetics Directive, and/or opacifying agents, such as pigments.

Although not obligatory, the composition can also comprise viscosifying or gelling polymers, so as to adjust the texture of the composition, such as crosslinked polyacrylates (Carbopol, sold by Goodrich), already mentioned above, non-cationic cellulose derivatives, such as hydroxypropylcellulose or carboxymethylcellulose, guars and their nonionic derivatives, xanthan gum and its derivatives, used alone or in combination, or the same compounds, generally in the form of water-soluble polymers modified by hydrophobic groups covalently bonded to the polymer backbone, as described in patent WO 92/16187, and/or water, in order to bring the total of the constituents of the formulation to 100%.

The cosmetic compositions forming the subject matter of the invention can also comprise polymeric dispersing agents in an amount of the order of 0.1-7% by weight, in order to control the calcium and magnesium hardness, agents such as:
  water-soluble salts of polycarboxylic acids with a weight-average molecular weight of the order of 2000 to 100 000 g/mol, obtained by polymerization or copolymerization of ethylenically unsaturated carboxylic acids, such as acrylic acid, maleic acid, maleic anhydride, fumaric acid, itaconic acid, aconitic acid, mesaconic acid, citraconic acid or methylenemalonic acid, and very particularly polyacrylates with a weight-average molecular weight of the order of 2000 to 10 000 g/mol (U.S. Pat. No. 3,308,067) or copolymers of acrylic acid and of maleic anhydride with a weight-average molecular weight of the order of 5000 to 75 000 g/mol (EP-A-66 915);
  polyethylene glycols with a weight-average molecular weight of the order of 1000 to 50 000 g/mol

Composition for Domestic, Industrial or Institutional Care Purposes

According to a specific embodiment, the composition is a composition (or "formulation") for domestic, industrial or institutional care purposes. It can in particular be a cleaning or rinsing composition.

The composition can be intended for the treatment of industrial, domestic or communal hard surfaces, in particular of ceramic, tiling, window, metal, melamine, formica or plastic type, targeted at conferring on the latter in particular persistent antideposition and/or antiadhesion properties with regard to soiling substances; in addition, it can contribute antistatic, gloss or slip-resistance properties to the latter.

The composition intended for the treatment of a hard surface is capable of conferring, on the latter, persistent antideposition and/or antiadhesion properties with regard to soiling substances, so as to prevent the subsequent presence of marks due in particular:
  to the drying of drops of water deposited on said surface (for example deposit of inorganic salts)
  to the attachment of inorganic or organic particles present in the surrounding air (case of the cleaning of skyscrapers) or deposited by contact (case of the cleaning of floors, toilets, and the like)
  to the deposition by spattering of fatty organic compounds (cooking fats)
  to the deposition of soaps and their metal salts
  to the deposition of compounds of vegetable origin of hydrocolloid or polysaccharide type.

The term "persistent antideposition and/or antiadhesion properties" is understood to mean that the treated surface retains these properties over time, including after subsequent contacts with a soiling substance (for example rainwater, water from the distribution network, rinsing water to which rinsing products have or have not been added, spattered fats, soaps, and the like). This property of persistence can be observed beyond approximately 10 rinsing cycles, indeed even, in some specific cases where numerous rinsings are carried out (case of toilets, for example), beyond 100 rinsing cycles.

The above expression of "conferring, on the surface thus treated, antideposition properties" means more particularly that the treated surface, brought into contact with a soiling substance in a predominantly aqueous medium, will not have a tendency to "capture" said soiling substance, which thus significantly reduces the deposition of the soiling substance on the surface.

The above expression of "conferring, on the surface thus treated, antiadhesion properties" means more particularly that the treated surface is capable of interacting only very slightly with the soiling substance which has been deposited thereon, which makes possible easy removal of the soiling substances from the soiled treated surface; this is because, during the drying of the soiling substance brought into contact with the treated surface, the bonds developed between the soiling substance and the surface are very weak; thus, to break these bonds requires less energy (thus less effort) during the cleaning operation.

When it is said that the presence of the copolymer makes it possible "to improve the cleaning ability" of a formulation, this means that, for the same amount of cleaning formulation (in particular a formulation for washing dishes by hand), the formulation comprising the copolymer makes it possible to clean a greater number of soiled objects than a formulation which is devoid thereof.

In addition, the deposition on a hard surface of the copolymer makes it possible to contribute antistatic properties to this surface; this property is particularly advantageous in the case of synthetic surfaces.

The presence of the copolymer in formulations for the treatment of a hard surface makes it possible to render the surface hydrophilic or to improve its hydrophilicity.

The property of hydrophilization of the surface makes it possible in addition to reduce the formation of condensation on the surface; this advantage can be made use of in cleaning formulations for windows and mirrors, in particular in bathrooms. Furthermore, the rate of drying of the surface, immediately after treatment thereof by the application of the polymer but also after subsequent and repeated contacts with an aqueous medium, is very significantly improved.

The term "hard surfaces" is to be taken in the broad sense; it refers to nontextile surfaces which can equally well be domestic, communal or industrial surfaces.

They can be made of any material, in particular of the following types:
  ceramic (surfaces such as bathroom sinks, bath tubs, wall or floor tiles, toilet bowls and the like),
  glass (surfaces such as interior or exterior windows of buildings or of vehicles, or mirrors,
  metal (surfaces such as internal or external walls of reactors, blades, panels, pipes, and the like), synthetic resins (for example bodywork or interior surfaces of motorized vehicles (automobiles, trucks, buses, trains, planes, and the like), melamine or formica surfaces for the interior of offices, kitchens, and the like),
plastics (for example polyvinyl chloride or polyamide, for the interior of vehicles, in particular automobiles).

The "hard surfaces" according to the invention are surfaces which are not very porous and which are non-fibrillate; they are thus to be distinguished from textile surfaces (fabrics, fitted carpets, clothes, and the like, made of natural, artificial or synthetic materials).

The composition according to the invention, capable of contributing, to the hard surfaces to be treated, antideposition and/or antiadhesion properties with regard to soiling substances, can be:

a composition for domestic use; it can be universal or can be more specific, such as a composition for cleaning or rinsing the bathroom; said composition prevents in particular deposition of soap salts around bath tubs and on bathroom sinks, prevents the growth and/or the deposition of calcium crystals on these surfaces, and delays the appearance of subsequent soap stains;

the kitchen; said composition makes it possible to improve the cleaning of worktops when the latter are soiled by unsaturated fatty soiling substances capable of crosslinking over time; the greasy stains come off with water without rubbing;

floors (made of linoleum, tiling or cement); said composition makes it possible to improve the removal of dust or soiling substances of argilo-calcareous types (soil, sand, mud, and the like); stains on the floor can be cleaned without effort by simple sweeping, without brushing; in addition, said composition contributes slip-resistance properties;

toilet bowls; said composition makes it possible to prevent the adhesion of traces of excrement to the surface; the flow alone of the flush of water is sufficient to remove these traces; the use of a brush is unnecessary;

windows or mirrors; said composition makes it possible to prevent the deposition of inorganic or organic particulate soiling substances on the surface;

dishes, by hand or using an automatic device; said composition makes it possible, in the case of washing by hand, to facilitate the removal of the residual stains from dried foods and to wash a larger number of items of cutlery or utensils with the same volume of washing medium; the surface of the still wet items of cutlery and utensils is no longer slippery and thus does not escape from the hands of the user; a squeaky clean effect has also been observed, namely that the surface "squeaks" under the effect of rubbing with the finger. In the case of washing or rinsing in a dishwasher, said composition makes possible the antiredeposition of soiling substances originating from foodstuffs and of insoluble inorganic calcium salts, and contributes shininess to the utensils and items of cutlery; the composition also makes it possible no longer to have to "prewash" the items of cutlery or utensils before they are introduced into the dishwasher.

A composition for industrial or communal use; it can be universal or more specific, such as a composition for cleaning reactors, steel blades, sinks or tanks,
dishes,
exterior or interior surfaces of buildings,
windows of buildings, including apartment buildings,
bottles.

The composition according to the invention can be provided in any form and can be used in multiple ways. Thus, it can be in the form of a gelled or ungelled liquid to be deposited as such, in particular by spraying,
directly on the surfaces to be cleaned or rinsed, or
on a sponge or another substrate (woven or nonwoven article made of cellulose, for example) before being applied to the surface to be treated,
of a gelled or ungelled liquid to be diluted in water (optionally with the addition of another solvent) before being applied to the surface to be treated,
of a gelled or ungelled liquid held in a water-soluble bag,
of a foam,
of an aerosol,
of a liquid absorbed on an absorbent substrate made of an article which is woven or nonwoven in particular (wipe),
of a solid, in particular a tablet, optionally held in a water-soluble bag, it being possible for said composition to represent all or part of the tablet.

For satisfactory implementation of the invention, the copolymer is present in the composition forming the subject matter of the invention in an amount which is effective in contributing, to said surfaces, antideposition and/or antiadhesion properties with regard to soiling substances capable of being deposited on said surfaces.

Said composition forming the subject matter of the invention can comprise, depending on its application, from 0.001 to 10% of its weight of the copolymer.

The pH of the composition or the pH of use of the composition according to the invention can vary, depending on the applications and the surfaces to be treated, from 1 to 14, indeed even from 0.5 to 14.

Extreme pH values are conventional in the applications of industrial or communal cleaning type. In the field of domestic applications, the pH values range instead from 1 to 13, depending on the applications.

Said composition can be employed for the cleaning or rinsing of hard surfaces in an amount such that, after optional rinsing and after drying, the amount of the copolymer deposited on the surface is from 0.0001 to 10 mg/m$^2$, preferably from 0.001 to 5 mg/m$^2$, of surface treated.

The composition according to the invention can additionally comprise at least one surface-active agent. The latter can be nonionic, anionic, amphoteric, zwitterionic or cationic. Surfactants of use have been mentioned above for the cosmetic compositions.

The surface-active agents can represent from 0.005 to 60%, in particular from 0.5 to 40%, of the weight of the composition of the invention, this being according to the nature of the surface-active agent(s) and the destination of the cleaning composition.

Advantageously, the copolymer/surface-active agent(s) ratio by weight is between 1/1 and 1/1000, advantageously 1/2 and 1/200.

The composition according to the invention can additionally comprise at least one other additive chosen in particular from conventional additives present in compositions for cleaning or rinsing hard surfaces.

Mention may in particular be made of:
chelating agents, in particular of the water-soluble aminophosphonates and organic phosphonates type, such as
1-hydroxyethane-1,1-diphosphonates,
aminotri(methylenediphosphonate),
vinyldiphosphonates, salts of oligomers or polymers of vinylphosphonic or vinyldiphosphonic acid, salts of random cooligomers or copolymers of vinylphosphonic or vinyldiphosphonic acid and of acrylic acid and/or of maleic anhydride and/or of vinylsulfonic acid and/or of acrylamidomethylpropane-sulfonic acid, salts of phosphonated polycarboxylic acids, polyacrylates comprising phosphonate ending(s), salts of cotelomers of vinylphosphonic or vinyldiphosphonic acid and of acrylic acid, such as those of the Briquest® range or Mirapol A300 or 400 from Rhodia (in a proportion of 0 to 10%, preferably of 0 to 5%, of the total weight of cleaning composition);

sequestering or scale-inhibiting agents, such as polycarboxylic acids or their water-soluble salts and water-soluble salts of carboxylic polymers or copolymers, such as polycarboxylate or hydroxypolycarboxylate ethers, polyacetic acids or their salts (nitriloacetic acid, N,N-dicarboxymethyl-2-aminopentanedioic acid, ethylenediaminetetraacetic acid, diethylenetriaminepentaacetic acid, ethylene-diaminetetraacetates, nitriloacetates or N-(2-hydroxyethyl)nitrilodiacetates), salts of ($C_5$-$C_{20}$ alkyl)succinic acids, polycarboxylic acetal esters, salts of polyaspartic or polyglutamic acids, citric acid, adipic acid, gluconic acid or tartaric acid, or their salts, copolymers of acrylic acid and of maleic anhydride or acrylic acid homopolymers, such as Rhodoline DP 226 35 from Rhodia and Sokalan CP5 from BASF (in a proportion of 0 to 10% of the total weight of said cleaning composition), sulfonated polyvinylstyrenes or their copolymers with acrylic acid, methacrylic acid, and the like, (in a proportion of 0 to 10% of the total weight of cleaning composition);

inorganic builders (detergency adjuvants which improve the surface properties of surfactants) of the type:

alkali metal, ammonium or alkanolamine polyphosphates, such as Rhodiaphos HD7, sold by Rhodia (in a proportion of 0 to 70% of the total weight of cleaning composition), alkali metal pyrophosphates, alkali metal silicates with an $SiO_2$/$M_2O$ ratio which can range from 1 to 4, preferably from 1.5 to 3.5, very particularly from 1.7 to 2.8; they can be amorphous silicates or lamellar silicates, such as the α, β, γ and δ phases of $Na_2Si_2O_5$, sold under the references NaSKS-5, NaSKS-7, NaSKS-11 and NaSKS-6 by Clariant, alkali metal or alkaline earth metal borates, carbonates, bicarbonates or sesquicarbonates (in an amount which can range up to approximately 50% of the total weight of said cleaning composition), cogranules of alkali metal silicate hydrates, with an $SiO_2$/$M_2O$ ratio which can range from 1.5 to 3.5, and of alkali metal (sodium or potassium) carbonates; mention may in particular be made of the cogranules in which the content by weight of water associated with the silicate with respect to the dry silicate is at least 33/100, it being possible for the ratio by weight of the silicate to the carbonate to range from 5/95 to 45/55, preferably from 15/85 to 35/65, such as described in EP-A-488 868 and EP-A-561 656, for example Nabion 15, sold by Rhodia, (it being possible for the total amount of builders to represent up to 90% of the total weight of said cleaning or rinsing composition);

bleaching agents of the perborates or percarbonates type, which may or may not be combined with acetylated bleaching activators, such as N,N,N',N'-tetraacetylethylenediamine (TAED), or chlorinated products of the chloroisocyanurates type, or chlorinated products of the alkali metal hypochlorites type, or aqueous hydrogen peroxide solution (in a proportion of 0 to 30% of the total weight of said cleaning composition);

fillers of the sodium sulfate, sodium chloride, sodium carbonate, calcium carbonate, kaolin or silica type, in a proportion of 0 to 50% of the total weight of said composition;

bleaching catalysts comprising a transition metal, in particular iron, manganese and cobalt complexes, such as those of the type $[Mn^{IV}_2(\mu\text{-}O)_3(Me_3TACN)_2](PF_6)_2$, $[Fe^{II}(MeN_4py)(MeCN)](ClO_4)_2$, $[(Co^{III})(NH_3)_5(OAc)](OAc)_2$, described in U.S. Pat. Nos. 4,728,455, 5,114,606, 5,280,117, EP-A-909 809, U.S. Pat. No. 5,559,261, WO 96/23859, 96/23860 and 96/23861 (in a proportion of 0 to 5% of the total weight of said cleaning composition);

agents which influence the pH of the composition, which are soluble in the cleaning or rinsing medium, in particular basifying additives (alkali metal phosphates, carbonates, perborates or alkali metal hydroxides) or optionally cleaning acidifying additives, such as inorganic acids (phosphoric, polyphosphoric, sulfamic, hydrochloric, hydrofluoric, sulfuric, nitric or chromic acid), carboxylic or polycarboxylic acids (acetic, hydroxyacetic, adipic, citric, formic, fumaric, gluconic, glutaric, glycolic, malic, maleic, lactic, malonic, oxalic, succinic and tartaric acid), or salts of acids, such as sodium bisulfate or alkali metal bicarbonates and sesquicarbonates;

polymers used to control the viscosity of the mixture and/or the stability of the foams formed during use, such as cellulose derivatives or guar derivatives (carboxymethylcellulose, hydroxyethylcellulose, hydroxypropyl guar, carboxymethyl guar, carboxymethyl hydroxypropyl guar, and the like), xanthan gum, succinoglycan (Rheozan® sold by Rhodia), locust bean gum or carrageenans (in a proportion of 0 to 2% of the total weight of said cleaning composition);

hydrotropic agents, such as short-chain $C_2$-$C_8$ alcohols, in particular ethanol, diols and glycols, such as diethylene glycol or dipropylene glycol, sodium xylenesulfonate or sodium naphthalenesulfonate (in a proportion of 0 to 10 g per 100 g of said cleaning composition);

moisturizing agents or humectants for the skin, such as glycerol or urea, or agents for protecting the skin, such as proteins or protein hydrolysates, vegetable oils, such as soybean oil, or cationic polymers, such as cationic guar derivatives (Jaguar C13S®, Jaguar C162® or Hicare 1000®, sold by Rhodia) (in a proportion of 0 to 40% of the total weight of said cleaning composition);

biocides or disinfectants, such as cationic biocides, for example mono(quaternary ammonium) salts, such as cocoalkylbenzyldimethylammonium, ($C_{12}$-$C_{14}$ alkyl)-benzyldimethylammonium, cocoalkyldichlorobenzyldimethylammonium, tetradecylbenzyldimethylammonium, didecyldimethylammonium or dioctyldimethylammonium chlorides, myristyltrimethylammonium or cetyltrimethylammonium bromides, monoquaternary heterocyclic amine salts, such as laurylpyridinium, cetylpyridinium or ($C_{12}$-$C_{14}$ alkyl)-benzylimidazolium chlorides, (fatty alkyl)triphenylphosphonium salts, such as myristyltriphenylphosphonium bromide, polymeric biocides, such as those derived from the reaction of epichlorohydrin and of dimethylamine or of diethylamine, of epichlorohydrin and of imidazole, of 1,3-dichloro-2-propanol and of dimethylamine, of 1,3-dichloro-2-propanol and of 1,3-bis(dimethylamino)-2-propanol, of ethylene dichloride and of 1,3-bis(dimethylamino)-2-propanol, of bis(2-chloroethyl)ether and of N,N'-bis(dimethyl-aminopropyl)urea or -thiourea, biguanidine polymer hydrochlorides, such as Vantocil IB, amphoteric biocides, such as N—[N'—($C_8$-$C_{18}$ alkyl)-3-aminopropyl]glycine, N—{N'—[N'''—($C_8$-$C_{18}$ alkyl)-2-aminoethyl]-2-aminoethyl}glycine or N,N-bis[N'—($C_8$-$C_{18}$ alkyl)-2-aminoethyl]glycine derivatives, such as (dodecyl)(aminopropyl)glycine or (dodecyl)(diethylenediamine)glycine, amines, such as N-(3-aminopropyl)-N-dodecyl-1,3-propanediamine, halogenated biocides, such as iodophores and hypochlorite salts, such as sodium dichloroisocyanurate, phenolic biocides, such as phenol, resorcinol, cresols or salicylic acid, hydrophobic biocides, such as para-chloro-meta-xylenol or dichloro-meta-xylenol, 4-chloro-m-cresol, resorcinol monoacetate, mono- or polyalkyl or -aryl phenols, cresols or resorcinols, such as o-phenylphenol, p-tert-butylphenol, or 6-(n-amyl)-m-cresol, alkyl and/or aryl chloro- or bromophenols, such as o-benzyl-p-chlorophenol, halogenated diphenyl ethers, such as 2',4,4'-trichloro-2-hydroxydiphenyl ether (triclosan) or 2,2'-dihydroxy-5,5'-dibromodiphenyl ether, chlorphenesin (p-chlorophenyl glyceryl ether), in a proportion of 0 to 50% of the total weight of said cleaning composition;

solvents having a good cleaning or degreasing activity, such as alkylbenzenes of octylbenzene type, olefins having a boiling point of at least 100° C., such as α-olefins, preferably 1-decene or 1-dodecene, glycol ethers of general formula R1O(R2O)$_m$H, where R1 is an alkyl group exhibiting from 3 to 8 carbons and each R2 is either an ethylene or propylene and m is a number which varies from 1 to 3; mention may be made of monopropylene glycol monopropyl ether, dipropylene glycol monobutyl ether, monopropylene glycol monobutyl ether, diethylene glycol monohexyl ether, monoethylene glycol monohexyl ether, monoethylene glycol monobutyl ether and their mixtures, diols exhibiting from 6 to 16 carbon atoms in their molecular structure; diols are particularly advantageous as, in addition to their degreasing properties, they can help in removing calcium salts (soaps); diols comprising from 8 to 12 carbon atoms are preferred, very particularly 2,2,4-trimethyl-1,3-pentanediol, other solvents, such as pine oil, orange terpenes, benzyl alcohol, n-hexanol, phthalic esters of alcohols having 1 to 4 carbon atoms, butoxy propanol, Butyl Carbitol and 1-(2-(n-butoxy)-1-methylethoxy)propan-2-ol, also known as butoxypropoxy propanol or dipropylene glycol monobutyl ether, diglycol hexyl (Hexyl Carbitol), butyl triglycol, diols, such as 2,2,4-trimethyl-1,3-pentanediol, and their mixtures, (in a proportion of 0 to 30% of the total weight of said cleaning composition);

industrial cleaners, such as solutions of alkali metal salts of the phosphate, carbonate, silicate, and the like, type of sodium or potassium (in a proportion of 0 to 50% of the total weight of said cleaning composition);

water-soluble organic solvents with little cleaning effect, such as methanol, ethanol, isopropanol, ethylene glycol, propylene glycol and their mixtures (in a proportion of 0 to 40% of the total weight of said cleaning composition);

cosolvents, such as monoethanolamide and/or β-aminoalkanols, which are particularly advantageous in compositions with a pH of greater than 11, very particularly of greater than 11.7, as they help in reducing the formation of films and marks on hard surfaces (they can be employed in a proportion of 0.05 to 5% of the weight of the cleaning composition); solvent systems comprising monoethanolamide and/or β-aminoalkanols are described in U.S. Pat. No. 5,108,660;

antifoaming agents, such as soaps in particular. Soaps are alkali metal salts of fatty acids, in particular sodium, potassium, ammonium and alkanol-ammonium salts of higher fatty acids comprising approximately from 8 to 24 carbon atoms and preferably from approximately 10 to approximately 20 carbon atoms; mention may in particular be made of mono-, di- and triethanolamine, sodium and potassium salts of mixtures of fatty acids derived from coconut oil and from ground walnut oil. The amount of soap can be at least 0.005% by weight, preferably from 0.5 to 2% by weight, with respect to the total weight of the composition. Additional examples of foam modifiers are organic solvents, hydrophobic silica, silicone oil and hydrocarbons.

abrasives, such as silica or calcium carbonate;

various additives, such as enzymes, fragrances, colorants, agents which inhibit corrosion of metals, preservatives, optical brighteners, opacifying or pearlescent agents, and the like.

The pH of the composition forming the subject matter of the invention or the pH of use of said composition can range from 0.5 to 14, preferably from 1 to 14.

Compositions of alkaline type, with a pH of greater than or equal to 7.5, preferably of greater than 8.5, for domestic applications (very particularly with a pH from 8.5 to 12, in particular from 8.5 to 11.5) are of particular use for the removal of greasy soiling substances and are particularly well suited to the cleaning of kitchens.

They can comprise from 0.001 to 5%, preferably from 0.005 to 2%, of their weight of the copolymer.

The alkaline compositions generally comprise, in addition to the copolymer, at least one additive chosen from a sequestering or scale-inhibiting agent (in an amount ranging from 0 to 40%, preferably from 1 to 40%, more preferably from 2 to 30% and very particularly from 5 to 20%, of the weight of the composition), a cationic biocide or disinfectant, in particular of quaternary ammonium type, such as (N-alkyl)benzyl-dimethylammonium chlorides, (N-alkyl)dimethyl(ethylbenzyl)ammonium chloride, N-didecyldimethylammonium halide and di(N-alkyl) dimethylammonium chloride (in an amount which can range from 0 to 60%, preferably from 0 to 40%, more preferably from 0 to 15% and very particularly from 0 to 5%, of the weight of the composition), at least one nonionic, amphoteric, zwitterionic or anionic surface-active agent or their mixture; when a cationic surface-active agent is present, said composition in addition preferably comprises an amphoteric and/or nonionic surface-active agent (the total amount of surface-active agents can range from 0 to 80%, preferably from 0 to 50%, very particularly from 0 to 35%, of the weight of the composition), if necessary, a pH modifier, in an amount which makes it possible to achieve, optionally after diluting or dissolving the composition, a pH of use ranging from 7.5 to 13; the pH modifier can in particular be a buffer system comprising monoethanolamine and/or a β-aminoalkanol and potentially but preferably "cobuffer" alkaline materials from the group consisting of aqueous ammonia, $C_2$-$C_4$ alkanolamines, silicates, borates, carbonates, bicarbonates, alkali metal hydroxides and their mixtures. The preferred cobuffers are alkali metal hydroxides.

from 0.5 to 98%, preferably from 25 to 95%, very particularly from 45 to 90%, by weight of water, a cleaning or degreasing organic solvent, in an amount which can represent from 0 to 60%, preferably from 1 to 45%, very particularly from 2 to 15%, of the weight of said composition, a cosolvent, such as monoethanolamine and/or β-aminoalkanols, in an amount which may represent from 0 to 10%, preferably from 0.05 to 10%, very particularly from 0.05 to 5%, by weight of said composition, a water-soluble organic solvent with little cleaning effect, in an amount which can represent from 0 to 25%, preferably from 1 to 20%, very particularly from 2 to 15%, of the weight of said composition, optionally a bleaching agent, a fragrance or other conventional additives.

Said alkaline compositions can be provided in the form of a ready-for-use formulation or else of a dry or concentrated formulation to be diluted in water in particular before use; they can be diluted from 1- to 10 000-fold, preferably from 1- to 1000-fold, before use.

Advantageously, a formulation for cleaning kitchens comprises:

from 0.001 to 1% by weight of the copolymer, from 1 to 10% by weight of water-soluble solvent, in particular isopropanol, from 1 to 5% by weight of cleaning or degreasing solvent, in particular butoxypropanol, from 0.1 to 2% by weight of monoethanolamine, from 0 to 5% by weight of at least one noncationic surface-active agent, preferably an amphoteric or nonionic surface-active agent, from 0 to 1% by weight of at least one cationic surface-active agent with a disinfecting property (in particular mixture of (n-alkyl)dimethyl(ethylbenzyl)-ammonium chloride and (n-alkyl)dimethylbenzylammonium chloride), the total amount of surface-active agent(s) representing from 1 to 50% by weight, from 0 to 2% by weight of a dicarboxylic acid as scale-inhibiting agent, from 0 to 5% of a bleaching agent, and from 70 to 98% by weight of water.

The pH of such a formulation is preferably from 7.5 to 13, more preferably from 8 to 12.

Compositions of acidic type, with a pH of less than 5, are of particular use for the removal of soiling substances of inorganic type; they are particularly well suited to the cleaning of toilet bowls.

They can comprise from 0.001 to 5%, preferably from 0.01 to 2%, of their weight of the copolymer.

The acidic compositions generally comprise, in addition to the copolymer, an inorganic or organic acidic agent (in an amount ranging from 0.1 to 40%, preferably from 0.5 to 20% and more preferably from 0.5 to 15%, of the weight of the composition), at least one nonionic, amphoteric, zwitterionic or anionic surface-active agent or their mixture (the total amount of surface-active agents can range from 0.5 to 20%, preferably from 0.5 to 10%, of the weight of the composition), optionally a cationic biocide or disinfectant, in particular of quaternary ammonium type, such as (N-alkyl)benzyldimethylammonium chloride, (N-alkyl)-dimethyl (ethylbenzyl)ammonium chloride, N-didecyl-dimethylammonium halide and di(N-alkyl)dimethylammonium chloride (in an amount which can range from 0.01 to 2%, preferably from 0.1 to 1%, of the weight of the composition), optionally a thickening agent (in an amount ranging from 0.1 to 3% of the weight of the composition), optionally a bleaching agent (in an amount ranging from 1 to 10% of the weight of the composition), from 0.5 to 99%, preferably from 50 to 98%, by weight of water, a solvent, such as glycol or an alcohol (in an amount which can range from 0 to 10%, preferably from 1 to 5%, of the weight of the composition), optionally a fragrance, a preservative, an abrasive or other conventional additives.

Said acidic compositions are preferably provided in the form of a ready-for-use formulation.

Advantageously, a formulation for cleaning toilet bowls comprises:

from 0.05 to 5%, preferably from 0.01 to 2%, by weight of the copolymer, an amount of acidic cleaning agent such that the final pH of the composition is from 0.5 to 4, preferably from 1 to 4; this amount is generally from 0.1 to approximately 40% and preferably between 0.5 and approximately 15% by weight, with respect to the weight of the composition; the acidic agent can be in particular an inorganic acid, such as phosphoric, sulfamic, hydrochloric, hydrofluoric, sulfuric, nitric or chromic acid and mixtures of these, an organic acid, in particular acetic, hydroxyacetic, adipic, citric, formic, fumaric, gluconic, glutaric, glycolic, malic, maleic, lactic, malonic, oxalic, succinic or tartaric acid and mixtures of these, or acid salts, such as sodium bisulfate, and mixtures of these; the preferred amount depends on the type of acidic cleaner used: for example, with sulfamic acid, it is between 0.2 and 10%, with hydrochloric acid between 1 and 15%, with citric acid between 2 and 15%, with formic acid between 5 and 15% and with phosphoric acid between 2 and 30%, by weight, from 0.5 to 10% by weight of at least one surface-active agent, preferably an anionic or nonionic surface-active agent, optionally from 0.1 to 2% by weight of at least one cationic surface-active agent with a disinfecting property (in particular mixture of (n-alkyl)dimethyl(ethylbenzyl)ammonium chloride and (n-alkyl)dimethylbenzylammonium chloride), optionally a thickening agent (in an amount ranging from 0.1 to 3% of the weight of the composition) of gum type, in particular a xanthan gum or a succinoglycan (Rheozan), optionally a bleaching agent (in an amount ranging from 1 to 10% of the weight of the composition), optionally a preservative, a colorant, a fragrance or an abrasive, and from 50 to 95% by weight of water.

A few other specific embodiments and forms of application of the composition of the invention are clarified below.

Thus, the composition according to the invention can be employed for making easier the cleaning treatment of glass surfaces, in particular of windows. This treatment can be carried out by the various known techniques. Mention may be made in particular of the techniques for cleaning windows by spraying with a jet of water using devices of the Kärcher® type.

The amount of copolymer introduced will generally be such that, during the use of the cleaning composition, after optional dilution, the concentration of copolymer is between 0.001 g/l and 2 g/l, preferably between 0.005 g/l and 0.5 g/l.

The composition for cleaning windows according to the invention comprises:

from 0.001 to 10%, preferably 0.005 to 3%, by weight of the copolymer;

from 0.005 to 20%, preferably from 0.5 to 10%, by weight of at least one nonionic surface-active agent (for example an amine oxide or an alkyl polyglucoside) and/or anionic surface-active agent; and the remainder being formed of water and/or of various additives which are conventional in the field.

The cleaning formulations for windows comprising said polymer can also comprise:

from 0 to 10%, advantageously from 0.5 to 5%, of amphoteric surfactant, from 0 to 30%, advantageously from 0.5 to 15%, of solvent, such as alcohols, the remainder being composed of water and of conventional additives (in particular fragrances).

The pH of the composition is advantageously between 6 and 11.

The composition of the invention is also advantageous for making easier the cleaning of dishes in an automatic device. Said composition can be either a detergent (cleaning) formulation used in the washing cycle or a rinsing formulation.

The detergent compositions for washing dishes in automatic dishwashers according to the invention advantageously comprise from 0.01 to 5%, preferably 0.1 to 3%, by weight of copolymer.

Said detergent compositions for dishwashers also comprise at least one surface-active agent, preferably a nonionic surface-active agent, in an amount which can range from 0.2 to 10%, preferably from 0.5 to 5%, of the weight of said detergent composition, the remainder being composed of various additives and of fillers, as already mentioned above.

Thus, they can additionally comprise up to 90% by weight of at least one detergency adjuvant (builder) of sodium tripolyphosphate or silicate type, up to 10%, preferably from 1 to 10%, very particularly from 2 to 8%, by weight of at least one auxiliary cleaning agent, preferably a copolymer of acrylic acid and of methylpropanesulfonic acid (AMPS), up to 30% by weight of at least one bleaching agent, preferably perborate or percarbonate, which may or may not be combined with a bleaching activator, up to 50% by weight of at least one filler, preferably sodium sulfate or sodium chloride.

The pH is advantageously between 8 and 13.

The compositions for making easier the rinsing of dishes in automatic dishwashers according to the invention can advantageously comprise from 0.02 to 10%, preferably from 0.1 to 5%, by weight of copolymer, with respect to the total weight of the composition.

Said compositions can also comprise from 0.1 to 20%, preferably 0.2 to 15%, by weight, with respect to the total weight of said composition, of a surface-active agent, preferably a nonionic surface-active agent.

Mention may be made, among preferred nonionic surface-active agents, of surface-active agents of the following types: polyoxyethylenated $C_6$-$C_{12}$ alkylphenols, polyoxyethylenated and/or polyoxypropylenated $C_8$-$C_{22}$ aliphatic alcohols, ethylene oxide/propylene oxide block copolymers, optionally polyoxyethylenated carboxamides, and the like.

Said compositions can additionally comprise from 0 to 10%, preferably from 0.5 to 5%, by weight, with respect to the total weight of the composition, of a calcium-sequestering organic acid, preferably citric acid.

They can also comprise an auxiliary agent of copolymer of acrylic acid and of maleic anhydride or acrylic acid homopolymers type, in a proportion of 0 to 15%, preferably 0.5 to 10%, by weight, with respect to the total weight of said composition.

The pH is advantageously between 4 and 7.

Another subject matter of the invention is a cleaning composition for making easier the washing of dishes b hand.

Preferred detergent formulations of this type comprise from 0.1 to 10 parts by weight of copolymer per 100 parts by weight of said composition and comprise from 3 to 50, preferably from 10 to 40, parts by weight of at least one surface-active agent, preferably an anionic surface-active agent, chosen in particular from sulfates of saturated $C_5$-$C_{24}$, preferably $C_8$-$C_{16}$, aliphatic alcohols, optionally condensed with approximately from 0.5 to 30, preferably 0.5 to 8, very particularly 0.5 to 5, mol of ethylene oxide, in the acid form or in the form of a salt, in particular an alkali metal (sodium) salt, alkaline earth metal (calcium, magnesium) salt, and the like.

Preferably, they are lathering liquid aqueous detergent formulations for making easier the washing of dishes by hand.

Said formulations can additionally comprise other additives, in particular other surface-active agents, such as:

nonionic surface-active agents, such as amine oxides, alkylglucamides, alkyl polyglucosides, oxyalkylenated derivatives of fatty alcohols, alkylamides or alkanolamides, or amphoteric or zwitterionic surface-active agents, noncationic bactericides or disinfectants, such as triclosan, synthetic cationic polymers, polymers for controlling the viscosity of the mixture and/or the stability of the foams formed during use, hydrotropic agents, moisturizing agents or humectants or agents for protecting the skin, colorants, fragrances, preservatives, divalent salts (in particular magnesium salts), and the like.

The pH of the composition is advantageously between 5 and 9.

Another specific embodiment of the invention is a composition for making easier the exterior cleaning, in particular of the bodywork, of motorized vehicles (automobiles, trucks, buses, trains, planes, and the like).

In this case also, the composition can be a cleaning composition proper or a rinsing composition.

The cleaning composition for motor vehicles advantageously comprises from 0.005 to 10% by weight of copolymer, with respect to the total weight of said composition, and:
- nonionic surface-active agents (in a proportion of 0 to 30%, preferably of 0.1 to 15%, of the formulation),
- amphoteric and/or zwitterionic surface-active agents (in a proportion of 0 to 30%, preferably of 0.01 to 10%, of the formulation),
- cationic surface-active agents (in a proportion of 0 to 30%, preferably of 0.5 to 15%, of the formulation),
- anionic surface-active agents (in a proportion of 0 to 30%, preferably of 0.1 to 15%, of the formulation),
- detergency adjuvants (builders) (in a proportion of 1 to 99%, preferably of 40 to 98%, of the formulation),
- hydrotropic agents,
- fillers, pH modifiers, and the like.

The minimum amount of surface-active agent present in this type of composition is preferably at least 0.5% of the formulation.

The pH of the composition is advantageously between 8 and 13.

The composition of the invention is also particularly suitable for making easier the cleaning of hard surfaces of ceramic type (tiling, bath tubs, bathroom sinks, and the like), in particular for bathrooms.

The cleaning formulation advantageously comprises from 0.02 to 5% by weight of copolymer, with respect to the total weight of said composition, and at least one surface-active agent.

Preference is given, as surface-active agents, to nonionic surface-active agents, in particular the compounds produced by condensation of alkylene oxide groups of hydrophilic nature with a hydrophobic organic compound which can be of aliphatic or alkylaromatic nature.

The length of the hydrophilic chain or of the polyoxyalkylene radical condensed with any hydrophobic group can be readily adjusted in order to obtain a water-soluble compound having the desired degree of hydrophilic/hydrophobic balance (HLB).

The amount of nonionic surface-active agents in the composition of the invention can be from 0 to 30% by weight, preferably from 0 to 20% by weight.

An anionic surfactant can optionally be present in an amount of 0 to 30%, advantageously 0 to 20%, by weight. It is also possible, but not essential, to add amphoteric, cationic or zwitterionic detergents.

The total amount of surface-active compounds employed in this type of composition is generally between 0.5 and 50%, preferably between 1 and 30%, by weight and more particularly between 2 and 20% by weight, with respect to the total weight of the composition.

Said cleaning composition can also comprise other minor ingredients, such as:
- detergency adjuvants (builders) as mentioned above (in an amount which can be between 0.1 and 25% by weight, with respect to the total weight of the composition),
- a foam modifier as mentioned above, in particular of soap type (in an amount generally of at least 0.005% by weight, preferably of 0.5% to 2% with respect to the total weight of the composition),
- pH modifiers, colorants, optical brighteners, agents for suspending soiling substances, detergent enzymes, compatible bleaching agents, agents for controlling gel formation, freezing-thawing stabilizers, bactericides, preservatives, solvents, fungicides, insect repellants, hydrotropic agents, fragrances and opacifying or pearlescent agents.

The pH of the composition is advantageously between 2 and 12.

The composition according to the invention is also suitable for making easier the rinsing of shower walls. The aqueous compositions for rinsing shower walls comprise from 0.02% to 5% by weight, advantageously from 0.05 to 1%, of the copolymer.

The other main active components of the aqueous compositions for rinsing showers of the present invention are at least one surface-active agent, present in an amount ranging from 0.5 to 5% by weight, and optionally a metal-chelating agent as mentioned above, present in an amount ranging from 0.01 to 5% by weight.

The aqueous compositions for rinsing showers advantageously comprise water with, optionally, a major proportion of at least one lower alcohol and a minor proportion of additives (between approximately 0.1 and approximately 5% by weight, more advantageously between approximately 0.5% and approximately 3% by weight and more preferably still between approximately 1% and approximately 2% by weight).

Some surface-active agents which can be used in this type of application are described in patents U.S. Pat. Nos. 5,536,452 and 5,587,022, the content of which is incorporated by reference in the present description.

Preferred surfactants are polyethoxylated fatty esters, for example polyethoxylated sorbitan monooleates and polyethoxylated castor oil. Specific examples of such surface-active agents are the condensation products of 20 mol of ethylene oxide and of sorbitan monooleate (sold by Rhodia Inc. under the name Alkamuls PSMO-20® with an HLB of 15.0) and of 30 or 40 mol of ethylene oxide and of castor oil (sold by Rhodia Inc. under the names Alkamuls EL-620® (HLB of 12.0) and EL-719® (HLB of 13.6) respectively). The degree of ethoxylation is preferably sufficient to obtain a surfactant with an HLB of greater than 13.

The pH of the composition is advantageously between 7 and 11.

The composition according to the invention can also be employed for making easier the cleaning of glass-ceramic sheets.

Advantageously, the formulations for cleaning glass-ceramic sheets of the invention comprise:
- 0.01 to 5% by weight of copolymer,
- 0.1 to 1% by weight of a thickener, such as a xanthan gum,
- 10 to 60% by weight of an abrasive agent, such as calcium carbonate or silica;
- 0 to 7% by weight of a solvent, such as butyl diglycol,
- 1 to 10% by weight of a nonionic surface-active agent, and optionally basifying agents or sequestering agents.

The pH of the composition is advantageously between 7 and 12.

As mentioned above, the composition according to the invention can also be employed in the field of industrial cleaning, in particular for making easier the cleaning of reactors.

Advantageously, said compositions comprise:
- from 0.02 to 5% by weight of copolymer,
- from 1 to 50% by weight of alkali metal salts (sodium or potassium phosphates, carbonates, silicates), from 1 to 30% by weight of a mixture of surface-active agents, in particular of nonionic surface-active agents, such as ethoxylated fatty alcohols, and anionic surface-active agents, such as laurylbenzenesulfonate, from 0 to 30% by weight of a solvent, such as diisobutyl ether.

The pH of such a composition is generally from 8 to 14.

Other details and advantages of the invention may become apparent in the light of the examples which follow, without a limiting nature.

EXAMPLES

Example 1

Preparation of an 80/20 by Moles Random Copolymer of SPP and of MAPTAC (p(SPP-stat-MAPTAC) 80/20)

150 g of SPP (Raschig), 56.62 g of a 50% by weight aqueous solution of MAPTAC (Röhm-Degussa) and 229.4 g of purified water are introduced, as vessel heel, at ambient temperature, into a 1 liter glass reactor equipped with a mechanical stirrer (Teflon anchor stirrer), a reflux condenser, a stainless steel temperature probe, a nitrogen inlet and a jacket connected to a thermostatically controlled bath. The reaction medium is placed under nitrogen (flushing) and brought to 80° C. in 1 h. At 80° C., an aqueous ammonium persulfate solution (0.1317 g in 10 g of purified water) is added to the reactor. The temperature of 80° C. and the stirring are maintained for 6 h.

Example 2

Preparation of a 90/10 by Moles Random Copolymer of SPP and of DIQUAT (p(SPP-stat-DIQUAT) 90/10)

150 g of SPP (Raschig), 31.4 g of a 65% by weight aqueous solution of DIQUAT and 234.8 g of purified water are introduced, as vessel heel, at ambient temperature, into a 1 liter glass reactor equipped with a mechanical stirrer (Teflon anchor stirrer), a reflux condenser, a stainless steel temperature probe, a nitrogen inlet and a jacket connected to a thermostatically controlled bath. The reaction medium is placed under nitrogen (flushing) and brought to 80° C. in 1 h. At 80° C., an aqueous ammonium persulfate solution (0.1171 g in 10 g of purified water) is added to the reactor. The temperature of 80° C. and the stirring are maintained for 6 h.

Example 3

Preparation of a 15/60/25 by Moles Random Copolymer of SPP, of Acrylamide (AM) and of DIQUAT (p(SPP-stat-AM-DIQUAT) 15/60/25)

50 g of SPP (Raschig), 97.24 g of a 50% by weight aqueous solution of AM (SNF-Floerger), 157 g of a 65% by weight aqueous solution of DIQUAT and 187.8 g of purified water are introduced, as vessel heel, at ambient temperature, into a 1 liter glass reactor equipped with a mechanical stirrer (Teflon anchor stirrer), a reflux condenser, a stainless steel temperature probe, a nitrogen inlet and a jacket connected to a thermostatically controlled bath. The reaction medium is placed under nitrogen (flushing) and brought to 80° C. in 1 h. At 80° C., an aqueous ammonium persulfate solution (0.2341 g in 10 g of purified water) is added to the reactor. The temperature of 80° C. and the stirring are maintained for 6 h.

Example 4

Preparation of an 80/20 by Moles Random Copolymer of SPE and of MAPTAC (p(SPE-stat-MAPTAC) 80/20)

150 g of SPE (Raschig), 59.3 g of a 50% by weight aqueous solution of MAPTAC (Röhm-Degussa) and 230 g of purified water are introduced, as vessel heel, at ambient temperature, into a 1 liter glass reactor equipped with a mechanical stirrer (Teflon anchor stirrer), a reflux condenser, a stainless steel temperature probe, a nitrogen inlet and a jacket connected to a thermostatically controlled bath. The reaction medium is placed under nitrogen (flushing) and brought to 80° C. in 1 h. At 80° C., an aqueous ammonium persulfate solution (0.1378 g in 10 g of purified water) is added to the reactor. The temperature of 80° C. and the stirring are maintained for 6 h.

Example 5 (Comparative)

Preparation of an SPE Homopolymer 150 g of SPE (Raschig) and 215.2 g of purified water are introduced, as vessel heel, at ambient temperature, into a 1 liter glass reactor equipped with a mechanical stirrer (Teflon anchor stirrer), a reflux condenser, a stainless steel temperature probe, a nitrogen inlet and a jacket connected to a thermostatically controlled bath. The reaction medium is placed under nitrogen (flushing) and brought to 80° C. in 1 h. At 80° C., an aqueous ammonium persulfate solution (0.1103 g in 10 g of purified water) is added to the reactor. The temperature of 80° C. and the stirring are maintained for 6 h.

Examples 6-15

Preparation of Shampoos Comprising the (Co)Polymers

Shampoo compositions are prepared which comprise ingredients chosen from the following:

| Starting material | Source | Nature |
| --- | --- | --- |
| SLES | Sodium lauryl ether sulfate (2 EO), Empicol ESB/3M, sold by Huntsman | Anionic surfactant |
| CAPB | Cocamidopropyl betaine, Mirataine BET-C-30, sold by Rhodia | Amphoteric surfactant |
| NaCl | | Salt |
| Polymer | Polymer according to examples 1 to 5 | |
| Silicone 1 | Mirasil DME-2, sold by Rhodia: dimethicone (PDMS) emulsion with a viscosity of approximately 500 000 cP, with a droplet size of approximately 2 µm, stabilized by succinoglycan | |

Procedure
1. The water and the polymer are mixed
2. The CAPB is added
3. The anionic surfactant and then, optionally, the silicone emulsion are added 4. The pH is adjusted to 6-6.5 by addition of sodium hydroxide or citric acid
5. The salt is added The following compositions are prepared, the amount by weight of each ingredient of which (on a dry basis) is given below (the letter C indicates comparative examples):

| Example | 6 | 7 | 8 | 9 | 10C |
|---|---|---|---|---|---|
| SLES (%) | 8 | 8 | 8 | 8 | 8 |
| CAPB (%) | 4 | 4 | 4 | 4 | 4 |
| NaCl (%) | 0.2 | 0.2 | 0.2 | 0.2 | 0.2 |
| Polymer | Example 1 0.2% | Example 2 0.2% | Example 3 0.2% | Example 4 0.2% | Example 5 0.2% |
| Water | | | Up to 100% | | |

| Example | 11 | 12 | 13 | 14 | 15C |
|---|---|---|---|---|---|
| SLES (%) | 8 | 8 | 8 | 8 | 8 |
| CAPB (%) | 4 | 4 | 4 | 4 | 4 |
| NaCl (%) | 0.2 | 0.2 | 0.2 | 0.2 | 0.2 |
| Silicone 1 (% on a dry basis) | 1 | 1 | 1 | 1 | 1 |
| Polymer | Example 1 0.2% | Example 2 0.2% | Example 3 0.2% | Example 4 0.2% | Example 5 0.2% |
| Water | | | Up to 100% | | |

Examples 16-17

Dilution Tests

The behavior of the compositions during dilution with water is studied by monitoring the transmittance.

The transmittance is measured using the Photometer 662 device from Metrohm at a wavelength of 600 nm on quartz cells with a width of 1 cm.

The measurement procedure during a dilution is as follows:
A dilution factor 2 corresponds to a dilution of one part by weight of test composition with one part by weight of water (1 part+1 part=dilution 2). The composition is placed in a beaker provided with a magnetic stirrer bar. The water is added thereto. The probe of the device for measuring the transmittance is placed in the mixture. The stirrer bar is put in motion so as to stir without creating bubbles (which might detrimentally affect the measurement of transmittance). After stirring for 5 minutes, the % of transmittance is recorded. This operation is repeated for a dilution factor 4 (1 part of composition per 3 parts of water), 6, 8 and the like. The transmittance at various degrees of dilution (dilution factor) is given in the table below.

| Dilution factor | Example 16 Transmittance, Composition of example 8 | Example 17 Transmittance, Composition of example 6 |
|---|---|---|
| 0 | 96.3 | 98.8 |
| 2 | 1 | 96.5 |
| 4 | 1.8 | 21.8 |
| 6 | 5.1 | 22.6 |
| 8 | 10.7 | 99.4 |

The fall in the transmittance corresponds to the formation of coacervatees. At high dilution, the coacervatees are completely destabilized and fall to the bottom of the cell. These coacervatees provide appropriate conditioning on the hair or an appropriate conditioning aid.

What is claimed is:
1. A random copolymer comprising:
zwitterionic units A comprising:

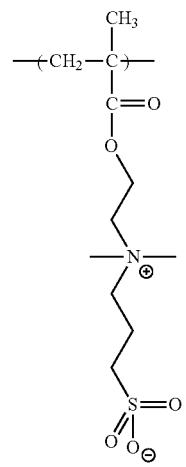

-(SPE)-

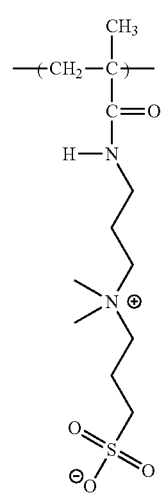

-(SPP)-

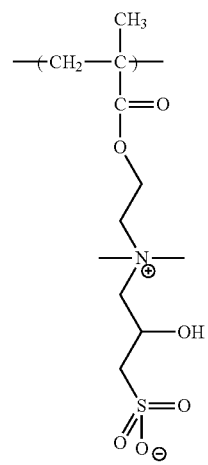

-(SHPE)-

-continued

-(SHPP)-

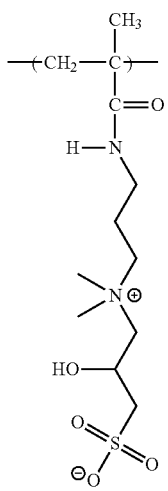

or a combination thereof; and cationic or potentially cationic units B comprising at least one quaternary ammonium group or at least one tertiary amine group.

2. The copolymer of claim 1, wherein the molar ratio of the units A to the units B is between 99/1 and 1/99.

3. The copolymer of claim 1, wherein the molar ratio of the units A to the units B is between 90/10 and 50/50.

4. The copolymer of claim 1, further comprising:
hydrophilic or hydrophobic nonionic units $C_N$, and/or
anionic or potentially anionic units $C_A$.

5. The copolymer of claim 1, wherein the units A and B represent from 1 to 100 mol %.

6. The copolymer of claim 1, wherein the units A and B represent from 1 to 95 mol %, of the units of the copolymer.

7. The copolymer of claim 1, wherein the units A and B, optionally with other units, form a polyalkylene hydrocarbon chain optionally interrupted by one or more nitrogen or sulfur atoms.

8. The copolymer of claim 1, wherein the units B are cationic or potentially cationic units comprising 1, 2, 3 or more cationic or potentially cationic groups in the chain forming the backbone of the copolymer or in the side position with respect to the chain forming the backbone of the copolymer.

9. The copolymer of claim 1, wherein the unit B comprises
N,N-dimethylaminomethylacrylamide or -methacrylamide,
[2-(N,N-dimethylamino)ethyl]acrylamide or -methacrylamide,
[3-(N,N-dimethylamino)propyl]acrylamide or -methacrylamide,
[4-(N,N-dimethylamino)butyl]acrylamide or -methacrylamide,
2-(dimethylamino)ethyl acrylate (ADAM),
2-(dimethylamino)ethyl methacrylate (DMAM),
3-(dimethylamino)propyl methacrylate,
2-(tert-butylamino)ethyl methacrylate,
2-(dipentylamino)ethyl methacrylate,
2-(diethylamino)ethyl methacrylate,
vinylpyridines,
vinylamine,
vinylimidazolines,
trimethylammoniopropyl methacrylate chloride,
trimethylammonioethylacrylamide or -methacrylamide chloride or bromide,
trimethylammoniobutylacrylamide or -methacryl-amide methyl sulfate,
trimethylammoniopropylmethacrylamidemethyl sulfate (IVIES),
(3-methacrylamidopropyl)trimethylammonium chloride (MAPTAC),
(3-acrylamidopropyl)trimethylammonium chloride (APTAC),
methacryloyloxyethyltrimethylammonium chloride or methyl sulfate,
acryloyloxyethyltrimethylammonium chloride or acryloyloxyethyltrimethylammonium methyl sulfate (ADAMQUAT Cl or ADAMQUAT MeS),
methyldiethylammonioethyl acrylate methyl sulfate (ADAEQUAT MeS),
benzyldimethylammonioethyl acrylate chloride or methyl sulfate (ADAMQUAT BZ 80),
1-ethyl-2-vinylpyridinium or 1-ethyl-4-vinyl-pyridinium bromide, chloride or methyl sulfate,
N,N-dimethyldiallylammonium chloride (DADMAC),
the chloride of dimethylaminopropyl-methacrylamide, N-(3-chloro2-hydroxypropyl)-trimethylammonium (DIQUAT chloride),
the methyl sulfate of dimethylamino-propylmethacrylamide, N-(3-(methyl, sulfate)-2-hydroxypropyl)trimethylammonium (DIQUAT methyl sulfate),
the monomer of formula:

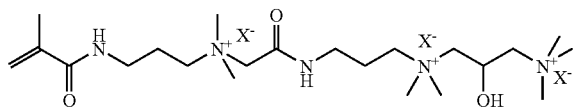

where $X^-$ is an anion, or
combinations thereof.

10. The copolymer of claim 4, wherein the copolymer comprises hydrophilic nonionic units $C_N$ that are derived from hydrophilic nonionic monomers $C_N$ that are:
hydroxyalkyl esters of α,β-ethylenically unsaturated acids;
α,β-ethylenically unsaturated amides;
α,β-ethylenically unsaturated monomers carrying a water-soluble polyoxyalkylene segment of the polyethylene oxide type;
α,β-ethylenically unsaturated monomers which are precursors of hydrophilic units or segments;
vinylpyrrolidones,
α,β-ethylenically unsaturated monomers of ureido type;
nonethylene glycol methyl ether acrylate or nonethylene glycol methyl ether methacrylate;
or combinations thereof.

11. The copolymer of claim 10, wherein the hydrophilic nonionic monomers $C_N$ are hydroxyethyl acrylate, hydroxyethyl methacrylate, hydroxypropyl acrylate, hydroxypropyl methacrylate, glycerol monomethacrylate, acrylamide, methacrylamide, N-methylolacrylamide, random or block polyethylene oxide and/or propylene oxide α-methacrylates, α,ω-dimethacrylates, ω-behenyl polyoxyethylene methacrylate, ω-tristyrylphenyl polyoxyethylene methacrylate, vinyl acetate, the methacrylamido of 2-imidazolidinone ethyl, or combinations thereof.

12. The copolymer of claim 1, wherein the copolymer comprises units A and B, and optionally acrylamide, wherein:

unit A comprises SPE or SPP and unit B comprises MAPTAC or DIQUAT.

13. The copolymer of claim 12, wherein:
unit A comprises 5 to 95 mol % of the copolymer and unit B comprises 5 to 95 mol % of the copolymer; or
unit A comprises 10 to 90 mol % of the copolymer and unit B comprises 10 to 90 mol % of the copolymer.

14. The copolymer of claim 12, wherein:
unit A comprises 5 to 90 mol % of the copolymer and unit B comprises 5 to 90 mol % of the copolymer; or
unit A comprises 10 to 80 mol % of the copolymer and unit B comprises 10 to 80 mol % of the copolymer; and
the acrylamide comprises 5 to 90 mol % of the copolymer; or
the acrylamide comprises 10 to 80 mol % of the copolymer.

15. The copolymer of claim 1, wherein the copolymer is water-soluble or water-dispersible.

16. A composition for the treatment or modification of surfaces, comprising:
a carrier
the copolymer of claim 1,
optionally a surfactant,
optionally a salt, an acid and/or a base, and
optionally an agent for the treatment or modification of the surface.

17. The composition of claim 16, wherein the surfactant is an anionic or amphoteric surfactant.

18. The composition of claim 16, wherein the units B are in the cationic form at the pH of the composition.

19. The composition of claim 16, wherein the composition:
comprises an anionic or amphoteric surfactant, and
the composition comprises coacervates or forms coacervates by dilution and/or modification of the pH of the composition.

20. A process for the treatment or modification of a surface, comprising the steps of:
applying, to the surface, the composition of claim 16, and
optionally removing the carrier, diluting the composition, or modifying the pH.

21. The composition of claim 1, wherein the zwitterionic units A comprise:
-(SHPE)-, -(SHPP)-, or a combination thereof.

* * * * *

UNITED STATES PATENT AND TRADEMARK OFFICE
CERTIFICATE OF CORRECTION

PATENT NO.       : 8,680,038 B2
APPLICATION NO.  : 12/097494
DATED            : March 25, 2014
INVENTOR(S)      : Balastre et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1179 days.

Signed and Sealed this
Twenty-ninth Day of September, 2015

Michelle K. Lee
*Director of the United States Patent and Trademark Office*